United States Patent [19]

Cox et al.

[11] 4,146,716
[45] Mar. 27, 1979

[54] THIENOPYRIMIDINES

[75] Inventors: John M. Cox, Wokingham; John H. E. Marsden, Manchester; Norman Elmore, Macclesfield; Margaret C. Shephard, Maidenhead; Raymond A. Burrell, Camberley, all of England

[73] Assignee: Imperial Chemical Industries Limited, London, England

[21] Appl. No.: 744,822

[22] Filed: Nov. 24, 1976

[30] Foreign Application Priority Data

Nov. 28, 1975 [GB] United Kingdom ............... 49025/75

[51] Int. Cl.$^2$ .......................................... C07D 239/00
[52] U.S. Cl. .................................. 544/278; 544/117; 424/251
[58] Field of Search ................... 260/256.5 R; 544/278

[56] References Cited

U.S. PATENT DOCUMENTS

| 3,470,183 | 9/1969 | Roth | 260/256.5 R |
| 3,475,429 | 10/1969 | Woitun et al. | 260/247.1 L |
| 3,763,156 | 10/1973 | Woitun et al. | 260/247.1 L |
| 3,850,919 | 11/1974 | Croisier et al. | 260/247.1 L |

FOREIGN PATENT DOCUMENTS

| 49-11895 | 2/1974 | Japan. |
| 49-13198 | 2/1974 | Japan. |
| 1057612 | 2/1967 | United Kingdom. |
| 1182507 | 2/1970 | United Kingdom. |
| 1277743 | 6/1972 | United Kingdom. |

OTHER PUBLICATIONS

Robba, Max et al., C. R. Acad. Sci., Paris, Ser. 1968, 266(2), Chemical Abstracts vol. 69: 27365j.
Robba, Max et al., C. R. Acad. Sci., Paris, Ser. 1968, 266(25), 1706-1708.
Robba et al., Bull. Soc. Chem. France, Part 2, 1975, (3-4), No. 111, pp. 592-597.
Bourguignon et al., Bull. Soc. Chem. France, Part 2, 1975, (3-4), No. 152, pp. 815-819.

Primary Examiner—Jose Tovar
Assistant Examiner—Lisa Jones
Attorney, Agent, or Firm—Cushman, Darby & Cushman

[57] ABSTRACT

Thienopyrimidines of the formula:

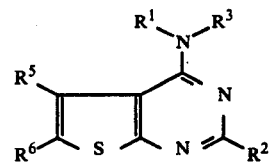

wherein $R^1$ is straight or branched chain alkyl containing from 3 to 11 carbon atoms and optionally substituted with cyano or methoxy, cycloalkyl, benzyl optionally substituted on the α carbon atom with a lower alkyl group or in the ring with one or more alkoxy groups or halogen atoms, dimethylamino, phenylethyl optionally substituted at the α- or β-carbon atoms with a lower alkyl group, tetrahydrofurfuryl; $R^3$ is hydrogen or $NH_2$; or $R^1$ and $R^3$ together form a carbon chain bridging group optionally saturated and containing one or more nitrogen atoms; $R^2$ is hydrogen, methyl, ethyl, or chlorine; $R^5$ is hydrogen or methyl; and $R^6$ is hydrogen, methyl or acetylamino; or an optical isomer thereof; or a tautomer thereof; or a salt thereof. These and other thienopyrimidines are disclosed as useful for plant growth regulation and for combating fungal, viral and bacterial diseases of plants and insect pests.

6 Claims, No Drawings

THIENOPYRIMIDINES

This invention relates to methods of combating pests, especially fungal, viral and bacterial infections of plants, and insect pests, by the use of certain thienopyrimidine derivatives; and to plant anti-fungal, anti-viral and anti-bacterial compositions; and to insecticidal and plant growth promoting compositions and to certain novel, specific, thienopyrimidine derivatives, and processes for making them.

The present invention provides a process for combating fungal, viral and bacterial diseases of plants and insect pests which comprises applying to plants, or to the locus of plants, an anti-fungal, anti-viral, anti-bacterial or insecticidal, amount of a thienopyrimidine derivative of the general formula:

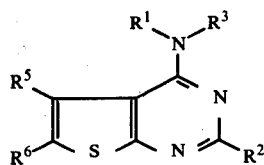

wherein $R^1$ and $R^3$ are hydrogen or optionally-substituted amino, alkyl, alkenyl, alkynyl, cycloalkyl, aralkyl, aryl or acyl groups, or together with the adjacent nitrogen atom form a heterocyclic group; $R^2$ is hydrogen, hydroxy, mercapto, halo, cyano, or optionally-substituted amino, hydrazino, alkyl, alkoxy, alkenyl, alkynyl, cycloalkyl, aralkyl, aryl, alkylthio, alkanesulphonyl or alkanesulphinyl, or is carboxylic-acid, -ester or -amide, or is a heterocyclic ring; $R^5$ and $R^6$ are hydrogen, halo, nitro, halosulphonyl, cyano, or optionally substituted alkyl, alkenyl, alkynyl, cycloalkyl, aralkyl, aryl, acyl, acylamino, aroyl, amino, acyloxy, amidosulphonyl, alkylthio or alkanesulphonyl groups or are carboxylic-acid, -ester, or -amide; or $R^5$ and $R^6$ together form a bridging group; or an optical isomer thereof; or a tautomer thereof; or a salt thereof.

In a preferred aspect the invention provides a process as stated above and wherein the thienopyrimidine has the general formula:

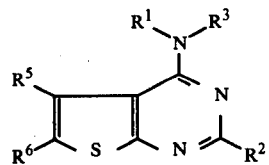

and wherein $R^1$ is hydrogen, allyl, propargyl, dimethylamino, acetyl, cycloalkyl, straight or branched chain alkyl containing from 1 to 14 carbon atoms optionally bearing one or more carboxyl, hydroxy, cyano, furyl, pyridyl, methoxy, mono- alkylamino, dialkylamino, phenyl optionally substituted with one or more halogen atoms, alkyl, or alkoxy, groups; $R^3$ is hydrogen, methyl, ethyl, phenyl, amino or acetyl; or $R^1$ and $R^3$ together represent a saturated or unsaturated bridging group optionally containing a nitrogen or oxygen atom; $R^2$ is hydrogen, methyl, ethyl, propyl, butyl, phenyl, trifluoromethyl, chlorine, imidazolyl, 1,2,4-triazol-1-yl, methoxy, hydrazino, amino, morpholino, pyrazolyl, 3,5-dimethyl pyrazolyl, azido, methylthio, piperidino, $SOCH_3$, $SO_2CH_3$, pyrrolidino, alkylamino, cyano, hydroxy, carboxy or mercapto; $R^5$ is hydrogen or methyl; $R^6$ is hydrogen, halogen, methyl, acetylamino, phenyl or nitro; or $R^5$ and $R^6$ together represent an alkylene bridge; or an optical isomer thereof; or a tautomer thereof; or a salt thereof.

In a more preferred aspect the invention provides a process as described above and wherein the thienopyrimidine has the general formula:

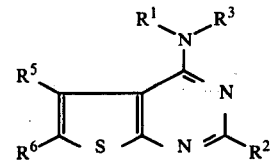

and wherein $R^1$ is straight or branched chain alkyl containing from 3 to 11 carbon atoms and optionally substituted with cyano or methoxy, cycloalkyl, benzyl optionally substituted on the α carbon atom with a lower alkyl group or in the ring with one or more alkoxy groups or halogen atoms, dimethylamino, phenylethyl optionally substituted at the α- or β-carbon atom with a lower alkyl group, tetrahydrofurfuryl; $R^3$ is hydrogen or $NH_2$; or $R^1$ and $R^3$ together form a carbon chain bridging group optionally saturated and containing one or more nitrogen atoms; $R^2$ is hydrogen, methyl, ethyl, or chlorine; $R^5$ is hydrogen or methyl; and $R^6$ is hydrogen, methyl or acetylamino; or an optical isomer thereof; or a tautomer thereof; or a salt thereof.

In an even more preferred aspect the invention provides a process as described above and wherein the thienopyrimidine has the general formula:

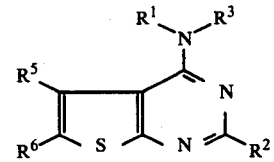

and wherein $R^2$ is H, halogen, methyl, ethyl or hydrazino; $R^3$ is hydrogen or amino; $R^5$ and $R^6$ are hydrogen or methyl, and $R^1$ is a straight or branched chain alkyl group optionally substituted with cyano or methoxy and containing from 3 to 11 carbon atoms, or a phenylmethyl or phenylethyl group optionally substituted at the α- or β-carbon atom with a lower alkyl group or on the phenyl ring with one or more methoxy groups or chlorine or fluorine atoms; or an optical isomer thereof; or a tautomer thereof; or a salt thereof.

In an even still more preferred aspect the invention provides a process as described above and wherein the thienopyrimidine derivative has the general formula:

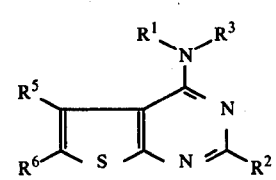

wherein $R^2$ is hydrogen, chlorine or methyl; $R^3$ is hydrogen; $R^5$ is hydrogen or methyl; $R^6$ is hydrogen; and $R^1$ is a straight or branched chain alkyl radical containing from 3 to 11 carbon atoms, or an α-alkyl substituted benzyl radical optionally substituted on the phenyl ring with halogen and containing up to 8 carbon atoms; or an optical isomer thereof; or a tautomer thereof; or a salt thereof.

In a particularly preferred aspect the invention provides a process for combatting fungal diseases of plants which comprises applying to plants, or to their locus, a thienopyrimidine derivative of the general formula:

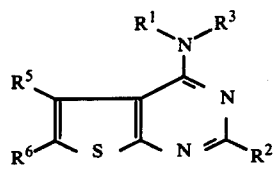

wherein $R^2$, $R^3$, $R^5$ and $R^6$ are hydrogen and $R^1$ is a straight or branched chain alkyl group containing from 3 to 8 carbon atoms, or is an α-alkyl substituted benzyl group; or an optical isomer thereof; or a tautomer thereof; or a salt thereof. Especially preferred thienopyrimidines for the foregoing process are those wherein $R^1$ is a branched chain alkyl group or an α-methyl substituted benzyl group.

The invention further provides thienopyrimidine derivatives; optical isomers thereof; tautomers thereof; and salts thereof as defined in any of the preceding four paragraphs.

The invention further provides a process for regulating the growth of plants which comprises applying to plants, or to the locus of plants, a thienopyrimidine derivative as defined in any of the preceding paragraphs.

In a further aspect the invention provides plant antifungal, anti-viral, and anti-bacterial and insecticidal compositions comprising as an active ingredient a thienopyrimidine derivative, or an optical isomer of a salt thereof, as defined in any of the preceding paragraphs; together with a carrier for the active ingredient; and optionally, a surface-agent.

Specific examples of thienopyrimidine derivatives according to the invention are set forth in Table I wherein the substituents $R^1$, $R^2$, $R^3$, $R^5$ and $R^6$ refer to the substituents in the general formula:

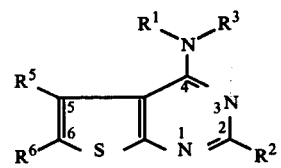

wherein the numbering of the ring atoms is as shown by the numbers inside the rings. The invention includes all those specific, novel, chemical compounds listed in Table I hereinafter.

TABLE 1

| Compound No. | $R^1$ | $R^2$ | $R^3$ | $R^5$ | $R^6$ | m.p. °C. |
|---|---|---|---|---|---|---|
| 1 | H | H | H | H | H | 235 |
| 2 | $CH_3$ | H | H | H | H | 202 |
| 3 | $CH_2CH_3$ | H | H | H | H | 162 |
| 4 | n-$C_3H_7$ | H | H | H | H | 136 |
| 5 | $CH(CH_3)_2$ | H | H | H | H | 228 |
| 6 | n-$C_4H_9$ | H | H | H | H | 106 |
| 7 | $CH(CH_3)C_2H_5$ | H | H | H | H | 192 |
| 8 | $CH_2$-furyl | H | H | H | H | 159 |
| 9 | $CH_2C_6H_5$ | H | H | H | H | 185 |
| 10 | n-$C_3H_7$ | H | H | H | $C_6H_5$ | 167 |
| 11 | n-$C_5H_{11}$ | H | H | H | H | 89 |
| 12 | $C_6H_5$ | H | H | H | H | 175 |
| 13 | n-$C_4H_9$ | H | H | H | $C_6H_5$ | 144 |
| 14 | H | H | H | $(CH_2)_4$ | | 263 |
| 15 | $CH_2C_6H_5$ | H | H | $(CH_2)_4$ | | 118 |
| 16 | $CH_2CH(CH_3)_2$ | H | H | H | H | 141 |
| 17 | cyclo hexyl | H | H | H | H | 174 |
| 18 | $CH(CH_3)_2$ | $CH_3$ | H | H | H | 166 |
| 19 | $(CH_2)_2OH$ | H | H | H | H | 179 |
| 20 | n-$C_6H_{13}$ | H | H | H | H | 59 |
| 21 | $CH(CH_3)C_2H_5$ | $CH_3$ | H | H | H | 179 |
| 22 | $CH_3$ | H | $CH_3$ | H | H | 76 |
| 23 | $CH_2C(CH_3)_3$ | H | H | H | H | 142 |
| 24 | $CH_2C_6H_5$ | $CH_3$ | H | H | H | 148 |
| 25 | $C(CH_3)_3$ | H | H | H | H | 172 |
| 26 | $C_2H_5$ | $CH_3$ | H | H | H | 162 |
| 27 | $CH_2CH_2C_6H_5$ | H | H | H | H | 189 |
| 28 | $CH_2CH=CH_2$ | H | H | H | H | 124 |
| 29 | cyclo heptyl | H | H | H | H | 128 |
| 30 | $CH(CH_3)C_6H_5$ | H | H | H | H | 132 |
| 31 | $CH_2$-4-pyridyl | H | H | H | H | 182 |
| 32 | $CH(CH_3)CH_2OCH_3$ | H | H | H | H | 153 |
| 33 | $CH(CH_3)CH_2CH(CH_3)_2$ | H | H | H | H | 138 |
| 34 | $CH_2CH(CH_2CH_3)(CH_2)_3CH_3$ | H | H | H | H | 72 |
| 35 | $CH(CH_3)(CH_2)_3CH(CH_3)_2$ | H | H | H | H | 104 |
| 36 | $CH(CH_3)C(CH_3)_3$ | H | H | H | H | 166 |
| 37 | $CH_2CH(CH_3)OH$ | H | H | H | H | 126 |
| 38 | $CH_2CH(OCH_3)_2$ | H | H | H | H | 101 |
| 39 | $CH_2CH_3$ | H | $CH_2CH_3$ | H | H | 73 |
| 40 | $CH(CH_3)(CH_2)_2CH_3$ | H | H | H | H | 120 |
| 41 | $(CH_2)_9CH_3$ | H | H | H | H | 52 |
| 42 | $CH_2C(OH)(CH_3)_2$ | H | H | H | H | 156 |
| 43 | $CH(CH_3)_2$ | $C_6H_5$ | H | H | H | 142 |
| 44 | $CH(CH_2CH_3)_2$ | H | H | H | H | 151 |
| 45 | $(CH_2)_2C(CH_3)_3$ | H | H | H | H | 135 |
| 46 | cyclo propyl | H | H | H | H | 146 |
| 47 | CH)$CH_3$)$CH(CH_3)_2$ | H | H | H | H | 134 |
| 48 | $CH(CH_3)CH_2CH_3$ | $C_5H_5$ | H | H | H | 142 |

TABLE 1-continued

| Compound No. | R¹ | R² | R³ | R⁵ | R⁶ | m.p. °C. |
|---|---|---|---|---|---|---|
| 49 | cyclo pentyl | H | H | H | H | 162 |
| 50 | CH₃ | H | C₆H₅ | H | H | 131 |
| 51 | CH₂C≡CH | H | H | H | H | 150 |
| 52 | CH₃ | H | (CH₂)₃CH₃ | H | H | [b.p.150° (bath)/ 0.03mm] |
| 53 | (CH₂)₃OCH₃ | H | H | H | H | 87 |
| 54 | CH[CH(CH₃)₂]₂ | H | H | H | H | 134 |
| 55 | CH₂C₆H₅ | C₆H₅ | H | H | H | 147 |
| 56 | CH(CH₃)(CH₂)₄CH₃ | H | H | H | H | 94 |
| 57 | (CH₂)₂CH(CH₃)₂ | H | H | H | H | 124 |
| 58 | CH₂CH(CH₃)CH₂CH₃ | H | H | H | H | 110 |
| 59 | cyclo butyl | H | H | H | H | 178 |
| 60 | (CH₂)₂N(CH₂CH₃)₂ | H | H | H | H | 88 |
| 61 | (CH₂)₁₁CH₃ | H | H | H | H | 61 |
| 62 | (CH₂)₂OCH₃ | H | H | H | H | 90 |
| 63 | CH₂-3-Cl—C₆H₄ | H | H | H | H | 174 |
| 64 | CH₂-2,4-Cl₂—C₆H₃ | H | H | H | H | 233 |
| 65 | (CH₂)₂N(CH₂CH₃)₂ | H | H | CH₃ | CH₃ | 75 |
| 66 | CH₂-4-OCH₃—C₆H₄ | H | H | H | H | 153 |
| 67 | CH₂-4-F—C₆H₄ | H | H | H | H | 139 |
| 68 | CH₂CH₂CH₃ | C₆H₅ | H | H | H | 85 |
| 69 | (CH₂)₅CN | H | H | H | H | 73 |
| 70 | CH₂-2-benzimidazolyl | H | H | H | H | >300 |
| 71 | CH₂-3,4-Cl₂—C₆H₃ | H | H | H | H | 166 |
| 72 | CH₂-2-Cl—C₆H₄ | H | H | H | H | 175 |
| 73 | CH₂-4-Cl—C₆H₄ | H | H | H | H | 174 |
| 74 | CH₂-cyclo hexyl | H | H | H | H | 136 |
| 75 | CH₂-3,4-(OCH₃)₂—C₆H₃ | H | H | H | H | 181 |
| 76 | (CH₂)₆CH₃ | H | H | H | H | 53 |
| 77 | cyclo octyl | H | H | H | H | 128 |
| 78 | (CH₂)₇CH₃ | H | H | H | H | 65 |
| 79 | CH(CH₃)-4-F—C₆H₄ | H | H | H | H | 150 |
| 80 | CH(C₆H₅)CH₂C₆H₅ | H | H | H | H | 149 |
| 81 | CH₂-4-CH₃—C₆H₄ | H | H | H | H | 144 |
| 82 | CH(CH₃)₂ | H | H | H | CH₃ | 163 |
| 83 | CH(CH₃)CH₂CH₃ | H | H | H | CH₃ | 170 |
| 84 | CH(CH₃)(CH₂)₄CH₃ | H | H | H | CH₃ | 152 |
| 85 | (CH₂)₂CH₃ | H | H | H | CH₃ | 147 |
| 86 | CH(C₆H₅)₂ | H | H | H | H | 107 |
| 87 | CH(CH₃)CH₂CH₃ | H | H | CH₃ | H | 129 |
| 88 | CH(CH₃)CH₂CH₃ | H | H | CH₃ | H | 70 |
| 89 | CH(CH₃)(CH₂)₄CH₃ | H | H | CH₃ | H | 77[b.p. 190° (bath)/ 0.05 mm] |
| 90 | CH₂CH(C₆H₅)₂ | H | H | H | H | 135 |
| 91 | CH₂-α-naphthyl | H | H | H | H | 174 |
| 92 | CH(CH₃)(CH₂)₇CH₃ | H | H | H | H | 105 |
| 93 | CH(CH₃)(CH₂)₂CH₃ | CH₃ | H | H | H | 132 |
| 94 | CH(CH₃)(CH₂)₄CH₃ | CH₃ | H | H | H | 107 |
| 95 | CH(CH₃)CH(CH₃)CH₂CH₃ | H | H | H | H | 128 |
| 96 | CH(CH₃)₂ | CF₃ | H | H | H | 102 |
| 97 | CH(CH₃)CH₂CH₃ | CF₃ | H | H | H | 73 |
| 98 | CH(CH₃)(CH₂)₄CH₃ | CF₃ | H | H | H | 85 |
| 99 | (CH₂)₂CH₃ | CF₃ | H | H | H | 75 |
| 100 | CH(CH₃)₂ | C(CH₃)₃ | H | H | H | 110 |
| 101 | C(CH₃)₂CH₂CH₃ | H | H | H | H | 106 |
| 102 | CH(CH₃)(CH₂)₂CH(CH₃)₂ | H | H | H | H | 106 |
| 103 | CH(CH₃)C₆H₅ | C(CH₃)₃ | H | H | H | 139 |
| 104 | CH(CH₃) (CH₂)₄CH₃ | C(CH₃)₃ | H | H | H | [b.p. 140° (bath)/ 0.01 mm] |
| 105 | CH(CH₃)C₆H₅ | CF₃ | H | H | H | 121 |
| 106 | CH₂-2,5-(CH₃)₂—C₆H₃ | H | H | H | H | 198 |
| 107 | CH(CH₃) (CH₂)₃CH₃ | H | H | H | H | 109 |
| 108 | CH(CH₃) (CH₂)₆CH₃ | H | H | H | H | 92 |
| 109 | CH(CH₃) (CH₂)₅CH₃ | H | H | H | H | 115 |
| 110 | CH[CH₂CH(CH₃)₂]₂ | H | H | H | H | 163 |
| 111 | CH₂-2,4-(OMe)₂—C₆H₃ | H | H | H | H | 151 |
| 112 | CH(CH₃) (CH₂)₄CH₃ | C₆H₅ | H | H | H | 96 |
| 113 | CH₃ | CF₃ | H | H | H | 134 |
| 114 | (CH₂)₂CH₃ | C(CH₃)₃ | H | H | H | 93 |
| 115 | CH(CH₃)CH₂CH₃ | C(CH₃)₃ | H | H | H | 131 |
| 116 | CH[(CH₂)₂CH₃]₂ | H | H | H | H | 147 |
| 117 | CH(CH₃)CH₂CH(CH₃)CH₂CH₃ | H | H | H | H | 136 |
| 118 | CH(CH₃)C₆H₅; prepared from (+) amine; R configuration | H | H | H | H | 120 |
| 119 | CH(CH₃)C₆H₅; prepared from (−) amine; S configuration | H | H | H | H | 120 |
| 120 | CH(CH₃) (CH₂)₃N(CH₂CH₃)₂ | H | H | H | H | 73 (monohydrate) |
| 121 | CH(CH₃)₂ | H | H | —(CH₂)₄— | | 135 |
| 122 | CH(CH₃)CH₂CH₃ | H | H | —(CH₂)₄— | | 153 |
| 123 | CH(CH₃)C₆H₅ | H | H | —(CH₂)₄— | | 142 |
| 124 | CH(CH₃) (CH₂)₃CH(CH₃)₂ | H | H | —(CH₂)₄— | | 65 |
| 125* | —(CH₂)₄— | H | (see R¹) | H | H | 90 |
| 126* | —CH=N—CH=CH— | H | (see R¹) | H | H | 177 |
| 127* | —CH=N—CH=N— | H | (see R¹) | H | H | 138 |
| 128* | —CH=CH—CH=N— | H | (see R¹) | H | H | 112 |

*Compounds Nos 125, 126, 127 and 128 have a combined R¹ and R³ bridging group shown complete under heading R¹.

| 129 | H | H | NH₂ | H | H | 225 |
| 130 | CH₃ | H | NH₂ | H | H | 173 |

TABLE 1-continued

| Compound No. | R¹ | R² | R³ | R⁵ | R⁶ | m.p. °C. |
|---|---|---|---|---|---|---|
| 131 | H | H | $NH_2$ | $CH_3$ | $CH_3$ | 219 |
| 132 | hydrochloride of compound No. 133 | | | | | 188 |
| 133 | $(CH_2)_2OH$ | H | $NH_2$ | H | $CH_3$ | 129 |
| 134 | $(CH_3)_2CH$ | H | H | H | $NO_2$ | 200 |
| 135 | $C_2H_5$ | H | $C_2H_5$ | H | $NO_2$ | 135 |
| 136 | $CH_2C_6H_5$ | H | H | H | $NO_2$ | 214 |
| 137 | $CH(CH_3)_2$ | Cl | H | H | H | 160 |
| 138 | $CH(CH_3)CH_2CH_3$ | Cl | H | H | H | 188 |
| 139 | $C_2H_5$ | Cl | H | H | H | 143 |
| 140 | $CH_3$ | Cl | H | H | H | 243 |
| 141 | $CH_2C_6H_5$ | Cl | H | H | H | 170 |
| 142 | $CH(CH_3)C_6H_5$ | Cl | H | H | H | 165 |
| 143 | $CH_2CH(CH_3)_2$ | Cl | H | H | H | 109 |
| 144* | $-(CH_2)_2O(CH_2)_2-$ | Cl | (see R¹) | H | H | 124 |
| 145 | $CH(CH_3)_2$ | imidazolyl | H | H | H | 228 |
| 146 | $CH(CH_3)_2$ | 1,2,4-triazol-1-yl | H | H | H | 192 |
| 147 | $CH(CH_3)_2$ | $OCH_3$ | H | H | H | 173 |
| 148 | $CH(CH_3)_2$ | $NHNH_2$ | H | H | H | 131 |
| 149 | $CH(CH_3)_2$ | morpholino | H | H | H | 173 |
| 150 | $CH(CH_3)_2$ | pyrazolyl | H | H | H | 198 |
| 151 | $CH(CH_3)_2$ | 3,5-dimethyl pyrazolyl | H | H | H | 233 |
| 152 | $CH(CH_3)_2$ | $N_3$ | H | H | H | 131 |
| 153 | $CH(CH_3)_2$ | $SCH_3$ | H | H | H | 128 |
| 154 | $CH(CH_3)_2$ | piperidino | H | H | H | 139 |
| 155 | $CH(CH_3)_2$ | $SO_2CH_3$ | H | H | H | 163 |
| 156 | $CH(CH_3)_2$ | pyrrolidino | H | H | H | 183 |
| 157 | $CH(CH_3)_2$ | $SOCH_3$ | H | H | H | 156 |
| 158 | $CH(CH_3)_2$ | $NHCH_2CH(CH_3)_2$ | H | H | H | 98 |
| 159 | $CH(CH_3)_2$ | CN | H | H | H | 168 |
| 160 | $CH(CH_3)_2$ | OH | H | H | H | 300 |
| 161 | $CH_2CH(CH_3)_2$ | OH | H | H | H | 239 |
| 162 | $CH(CH_3)_2$ | COOH | H | H | H | 187 |
| 163 | $CH(CH_3)_2$ | SH | H | H | H | 210 |
| 164* | $-(CH_2)_2O(CH_2)_2-$ | $NHCH_2CH(CH_3)_2$ | (see R¹) | H | H | 83 |
| 165 | $COCH_3$ | H | H | H | H | 190 |
| 166 | $COCH_3$ | H | $COCH_3$ | H | H | 103 |
| 167 | $CH(CH_3)_2$ | H | $COCH_3$ | H | H | 81–84 |
| 168 | $n-C_3H_7$ | H | $COCH_3$ | H | H | 48–53 |
| 169 | $CH_2CH(CH_3)_2$ | OH | $COCH_3$ | H | H | 147 |
| 170 | Hydrochloride salt of Compound No. 5 above | | | | | |
| 171 | Hydrochloride salt of Compound No. 104 above | | | | | |

*Compounds No 144 and 164 have a combined R¹ and R³ bridging group, shown complete under R¹

| Compound No. | R¹ | R² | R³ | R⁵ | R⁶ | m.p. °C. |
|---|---|---|---|---|---|---|
| 172 | $CH(CH_3)C_6H_5$ | $CH_3$ | H | H | H | 129 |
| 173 | $CH(CH_3)_2$ | $C_2H_5$ | H | H | H | 111 |
| 174 | $CH(CH_3)(CH_2)_{10}CH_3$ | H | H | H | H | 64 |
| 175 | 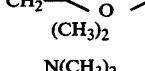 | H | H | H | H | 93 |
| 176 | $(CH_3)_2$ | H | $NH_2$ | H | H | 124 (chloride) |
| 177 | $N(CH_3)_2$ | H | H | H | H | 157 |
| 178 | $CH(CH_3)_2$ | H | H | $CH_3$ | $CH_3$ | 126 |
| 179 | $CH(CH_3)(CH_2)_2CH_3$ | H | H | $CH_3$ | $CH_3$ | 113 |
| 180 | $CH(CH_3)C_6H_5$ | H | H | $CH_3$ | $CH_3$ | 105 |
| 181 | $CH(CH_3)(CH_2)_4CH_3$ | H | H | $CH_3$ | $CH_3$ | 71 |
| 182 | $CH(CH_3)C_6H_5$ | $C_6H_5$ | H | H | H | 132 |
| 183 | $CH(CH_3)CH_2CN$ | H | H | H | H | 131 |
| 184 | 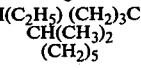 | H | H | H | H | 195 |
| 185 | $CH(C_2H_5)(CH_2)_3CH_3$ | H | H | H | H | 108 |
| 186 | $CH(CH_3)_2$ | H | H | H | $NHCOCH_3$ | 319 |
| 187 | $(CH_2)_5$ | H | $NH_2$ | H | H | 156 (chloride) |
| 188 | $C(CH_3)_2CH_2OH$ | H | H | H | H | 226 |
| 189 | $CH(C_2H_5)CH_2CH(CH_3)C_2H_5$ | H | H | H | H | 131 |
| 190 | $CH[(CH_2)_3CH_3]_2$ | H | H | H | H | 136 |
| 191 | 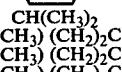 | H | H | H | H | 206 |
| 192 | $CH(CH_3)_2$ | $CH(CH_3)_2$ | H | H | H | 89 |
| 193 | $CH(CH_3)(CH_2)_2CH_3$ | Cl | H | H | H | 131 |
| 194 | $CH(CH_3)(CH_2)_2CH_3$ | $CH(CH_3)_2$ | H | H | H | 94 |
| 195 | $CH(CH_3)(CH_2)_4CH_3$ | $CH(CH_3)_2$ | H | H | H | [b.p. 150° (bath)/0.01 mm] |
| 196 | $(CH_2)_2CH_3$ | $CH(CH_3)_2$ | H | H | H | 75 |
| 197 | $CH(CH_3)C_6H_5$ | $CH(CH_3)_2$ | H | H | H | 123 |
| 198 | $CH[(CH_2)_4CH_3]_2$ | H | H | H | H | 89 |
| 199 | $CH(CH_3)(CH_2)_3CH_3$ | $CH_3$ | H | H | H | 118 |
| 200 | $CH(CH_3)(CH_2)_2CH(CH_3)_2$ | $CH_3$ | H | H | H | 122 |
| 201 | $CH(CH_3)C(CH_3)_3$ | Cl | H | H | H | 157 |
| 202 | $CH(CH_3)_2$ | $CH_3$ | H | $CH_3$ | H | 55 |
| 203 | $CH(CH_3)C_6H_5$ prepared (−) amine; S configuration | $CH_3$ | H | H | H | 119 |

TABLE 1-continued

| Compound No. | R¹ | R² | R³ | R⁵ | R⁶ | m.p. °C. |
|---|---|---|---|---|---|---|
| 204 | CH(CH₃) (CH₂)₄CH₃ | Cl | H | H | H | 91 |
| 205 | CH(CH₃) (CH₂)₃CH(CH₃)₂ | CH₃ | H | H | H | 113 |
| 206 | CH(CH₃) (CH₂)₅CH₃ | CH₃ | H | H | H | 109 |
| 207 | CH(CH₃) (CH₂)₆CH₃ | CH₃ | H | H | H | 89 |
| 208 | CH(CH₃) (CH₂)₇CH₃ | CH₃ | H | H | H | 72 |
| 209 | salt of Compound No 5 with sulphuric acid | | | | | 161 |
| 210 | salt of Compound No 5 with nitric acid | | | | | 147 |
| 211 | salt of Compound No 40 with hydrochloric acid | | | | | 173 |
| 212 | CH(CH₃) (CH₂)₂CH₃ | CH₃ | H | CH₃ | H | [b.p. 165° (bath)/0.01 mm] |
| 213 | salt of Compound No 40 with nitric acid | | | | | 115 |
| 214 | CH(CH₃) (CH₂)₄CH₃ | CH₃ | H | CH₃ | H | [b.p. 175° (bath)/0.01 mm] |
| 215 | salt of Compound No 5 with phosphoric acid | | | | | 211 |
| 216 | salt of Compound No 5 with toluene p-sulphonic acid | | | | | 168 |
| 217 | CH(CH₃) (CH₂)₂CH₃ | H | H | CH₃ | H | 79 [b.p. 165° (bath)/0.02 mm] |
| 218 | CH[(CH₂)₈CH₃]₂ | H | H | H | H | [b.p. 200° (bath)/0.03 mm] |
| 219 | salt of Compound No 5 with methanesulphonic acid | | | | | oil |
| 220 | salt of Compound No 5 with trichloroacetic acid | | | | | oil |
| 221 | salt of Compound No 40 with sulphuric acid | | | | | 100 |
| 222 | salt of Compound No 40 with toluene p-sulphonic acid | | | | | oil |
| 223 | 4—CH₃—C₆H₄ | H | H | H | H | 166 |
| 224 | 4—Cl—C₆H₄ | H | H | H | H | 157 |
| 225 | CH₂C₆H₅ | H | NH₂ | H | H | 149 |
| 226 | salt of Compound No 40 with phosphoric acid | | | | | 216 |
| 227 | CH(CH₃) (CH₂)₈CH₃ | H | H | H | H | 73 |
| 228 | CH(CH₃) (CH₂)₄CH₃ | 4-Cl—C₆H₄ | H | H | H | 105 |
| 229 | CH(CH₃)₂ | 4-Cl—C₆H₄ | H | H | H | 155 |
| 230 | (CH₂)₆NH— 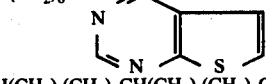 | H | H | H | H | 194 |
| 231 | CH(CH₃) (CH₂)₂CH(CH₃) (CH₂)₂CH₃ | H | H | H | H | 53 [b.p. 160° (bath)/0.02 mm] |
| 232 | CH(CH₃) (CH₂)₁₁CH₃ | H | H | H | H | 69 [b.p. 170° (bath)/0.04 mm] |
| 233 | CH(CH₃)C₆H₅ prepared from (−) amine; S configuration | C₂H₅ | H | H | H | 137 |
| 234 | CH(CH₃) (CH₂)₂CH₃ | 4-Cl—C₆H₄ | H | H | H | 120 |
| 235 | CH(CH₃) (CH₂)₂CH₃ | H | H | H | Br | 183 |
| 236 | CH(CH₃)₂ | H | H | H | Br | 186 |
| 237 | CH(CH₃)C₆H₅ | CH₃ | H | CH₃ | H | 119 [b.p. 210° (bath)/0.01 mm] |
| 238 | CH(CH₃)C₂H₅ | C₂H₅ | H | H | H | 109 |
| 239 | CH(CH₃) (CH₂)₂CH₃ | C₂H₅ | H | H | H | [b.p. 175° (bath/0.04 mm] |
| 240 | CH(CH₃) (CH₂)₄CH₃ | C₂H₅ | H | H | H | [b.p. 190° (bath)/0.04 mm] |
| 241 | CH(CH₃) (CH₂)₄CH₃ | H | H | H | Br | 153 |
| 242 | CH(CH₃)C₆H₅ | H | H | H | Br | 182 |
| 243 | CH(CH₃)CO₂H | H | H | H | H | 175 |
| 244 | (CH₂)₃N(CH₃)₂ | H | H | H | H | [b.p. 150° (bath)/0.04 mm] |
| 245 | CH(C₂H₅)₅CH₃ | H | H | H | H | 84 [b.p. 160° (bath)/0.05 mm] |
| 246 | CH(CH₃) (CH₂)₃CH₃ | C₂H₅ | H | H | H | 83 [b.p. 160° (bath)/0.06 mm] |
| 247 | CH(CH₃) (CH₂)₁₆CH₃ | H | H | H | H | 73 |
| 248 | CH(CH₃) (CH₂)₂CH(CH₃)₂ | C₂H₅ | H | H | H | 89 |
| 249 | CH(CH₃) (CH₂)₂CH₃ | C₂H₅ | H | H | H | 81 |
| 250 | CH(CH₃)₂ | H | H | H | (CH₃)₂NSO₂ | 202 |
| 251 | CH(CH₃) (CH₂)₂CH₃ | H | H | H | (CH₃)₂NSO₂ | 132 |
| 252 | CH(CH₃) (CH₂)₄CH₃ | H | H | H | (CH₃)₂NSO₂ | 135 |
| 253 | CH(CH₃)C₆H₅ | H | H | H | (CH₃)₂NSO₂ | 235 |
| 254 | CH(CH₃)₂ | SCH₂CONH₂ | H | H | H | 186 |

In the foregoing Table the following groups of Compounds are preferred groups but are progressively less preferred groups moving from group (i) through to group (v).

(i) 5, 7, 30, 40, 76, 109, 119
(ii) 21, 25, 33, 35, 44, 56, 79, 93, 94, 107, 108, 117, 137
(iii) 18, 20, 95, 101, 102, 185, 203, 206, 207
(iv) 32, 36, 41, 53, 54, 66, 69, 78, 87, 88, 89, 92, 116, 138, 148, 178, 183, 189, 193, 198
(v) 4, 24, 27, 49, 57, 59, 63, 67, 82, 111, 126, 129, 173, 175, 177, 186, 193, 202

All these compounds are new and, in particular as grouped, form preferred aspects of the present invention; together with pesticidal processes using them to combat fungal, viral and bacterial diseases of plants and insect pests; pesticidal compositions containing them; and new and/or analogous process herein described for making them.

The compounds of the invention, both novel and known, can be made either by:

(a) treating an appropriately substituted 2-amino-3-cyanothiophene with an orthoester, or a Vilsmeier reagent (e.g. N-N-dimethylformamide/phosphorus oxychloride), then an amine and rearranging the product, if necessary, with a strong base such as sodium alkoxide.

(b) reacting a thieno [2,3-d] pyrimidine containing a labile function (e.g. halo, mercapto, alkylthio, alkanesulphonyl) with an amine or a salt thereof.

(c) treating a 4-aminothieno [2,3-d] pyrimidine, if necessary under basic conditions, with a compound having an electrophilic centre.

(d) Subjecting a compound prepared as described above under (a), (b) or (c) to further reaction for example by replacement of halogen at C-2, nitration or halogenation of thiophene ring.

or (e) Treating 4-unsubstituted- or 4-monosubstituted-amino derivatives with acid halides or acid anhydrides, especially under basic conditions to give 4-acylamino thieno [2,3-d] pyrimidines.

The thienopyrimidine derivatives, and compositions containing them, are variously active against many fungal pathogens of plants and seeds including, for example, Phycomycetes, Ascomycetes, Basidiomycetes, and Fungi Imperfecti. The following diseases are specifically mentioned by way of example:

*Erysiphe graminis* (powdery mildew) on wheat and barley.

*Botrytis cinerea* (grey-mould) on tomatoes, vines, strawberries and other crops.

*Venturia inaequalis* (scab) on apples.

*Puccinia recondita* (rust) and other Puccinia species on cereals, and rusts on coffee and other hosts.

*Phytophthora infestans* (late blight) on tomatoes and potatoes.

*Plasmopara viticola* (downy mildew) on vines.

*Uncinula necator* (powdery mildew) on vines.

*Piricularia oryzae* (blast) on rice.

*Podosphaera leucotricha* (mildew) on apples.

The thienopyrimidine derivatives and compositions containing them also display properties influencing and regulating the growth of plants, and the present invention includes their deployment for this purpose.

The thienopyrimidine derivatives may be used as fungicides, viricides, bactericides or insecticides alone, but are preferably incorporated in compositions comprising a diluent in addition to the thienopyrimidine derivative.

For the control of both fungal, viral and bacterial infections of plants, the rate at which the thienopyrimidine compounds of the invention are applied will vary, depending upon the particular compound chosen for use, the disease to be controlled and on the particular species of plant acting as host to the disease.

In carrying the invention process into practical effect the growing crops, plants, seeds, or soil may be treated by any of the well-known and established procedures used in agriculture and crop protection. Thus, for example, the active compound may be applied as solids, e.g. powders or granules, or as liquids, e.g. solutions, dispersions, emulsions and these may comprise, in addition to the active substance, any other adjuvant, for example stickers, adjuvants specifically useful for formulation purposes, or any other biologically active substance, for example to increase the number of diseases combated, or having other desirable properties.

Such solid or liquid substances and formulations may be applied, for example, by any conventional technique, for example, by dusting, or otherwise applying the solid substances and formulations to the surfaces of growing crops, harvested produce, plants, seeds or soil, or to any part, or combination of parts thereof, or, for example, by applying liquids or solutions, for example, by dipping, spraying, mist-blowing or soaking techniques.

The invention process is therefore useful for treating plants, seeds, harvested fruits, vegetables, or cut flowers infested with, or liable to infestation with any of the aforementioned specific fungal or bacterial diseases.

The term "seeds" is intended to include propagative plant forms generally and therefore includes, for example, cut stems, corms, tubers, rhizomes and the like.

As previously noted the thienopyrimidine derivatives are preferably used in admixture with a solid or liquid diluent. The admixtures so obtained are hereinafter referred to as compositions. Preferably the compositions comprise a surface active-agent.

The solid compositions may be, for example, in the form of dusting powders, or may take the form of granules. Suitable solid diluents include, for example, kaolin, bentonite, kieselguhr, dolomite, calcium carbonate, talc, powdered magnesia and Fuller's earth.

Solid compositions may also be in the form of dispersible powders or grains comprising, in addition to the active ingredient, a wetting agent to facilitate the dispersion of the powder or grains in liquids. Such powders or grains may include fillers, suspending agents and the like.

Liquid compositions include aqueous solutions, dispersions and emulsions containing the active ingredient preferably in the presence of one or more surface-active agents. Water or organic liquids may be used to prepare solutions, dispersions, or emulsions of the active ingredient. The liquid compositions of the invention may also contain one or more corrosion inhibitors for example, lauryl isoquinolinium bromide.

Surface-active agents may be of the cationic, anionic or non-ionic type. Suitable agents of the cationic type include, for example, cetyltrimethyl ammonium bromide. Suitable agents of the anionic type include, for example, soaps, salts of aliphatic monoesters of sulphuric acid, for example, sodium lauryl sulphate; and salts of sulphonated aromatic compounds, for example, dodecylbenzenesulphonate, sodium, calcium and ammonium lignosulphonate, butylnaphthalene sulphonate, and a mixture of the sodium salts of diisopropy- and triisopropyl-naphthalenesulphonic acid. Suitable agents of the non-ionic type include, for example, the condensation products of ethylene oxide with fatty alcohols such as oleyl alcohol and cetyl alcohol, or with alkyl phenols such as octyl-phenol, nonylphenol and octyl-cresol. Other non-ionic agents are the partial esters derived from long chain fatty acids and hexitol anhydrides, for example, sorbitol monolaurate, and the condensation products of the said partial esters with ethylene oxide and the lecithins.

The compositions which are to be used in the form of aqueous solutions, dispersions or emulsions are generally supplied in the form of a concentrate containing a high proportion of the active ingredient, the concentrate being diluted with water before use. These concentrates are usually required to withstand storage for prolonged periods and after such storage to be capable of dilution with water in order to form aqueous preparations which remain homogenous for a sufficient time to enable them to be applied by conventional spray equipment. In general concentrates may conveniently contain from 10 to 85% and preferably from 25 to 60% by weight of active ingredient. One suitable form of concentrate is an emulsifiable concentrate comprising a solution of a thienopyrimidine derivative, as defined above, in an organic solvent containing a surface-active agent. When required for use, the concentrate can readily be dispersed in water by agitation to provide a dilute emulsion suitable for spraying. Dilute preparations ready for use may contain varying amounts of the active ingredient. depending upon the purpose for which they are to be used; however, dilute preparations may contain between 0.0005% and 0.1% by weight of the active ingredient.

It is to be understood that the pesticidal compositions used in this invention may comprise, in addition to one or more thienopyrimidine derivatives, one or more other compounds having biological activity.

The invention is illustrated, but not limited, by the following Examples, in which degrees of temperature signified by ° are expressed in degrees Centigrade. Examples 1 to 20 related to processes for the preparation of thienopyrimidine derivatives; Examples 21 to 29 to pesticidal compositions; and Examples 30 to 37 to processes for combating fungi, viruses, bacteria or insect pests.

EXAMPLE 1

This Example illustrates the preparation of compound nos. 1–15 of Table 1.

A mixture of an optionally substituted 2-amino-3-cyanothiophene (2.48 g) and triethylorthoformate (50 ml) was refluxed for four hours, then excess ester removed in vacuo. The residue was treated with a solution of an amine (excess) in ethanol, stirred overnight at room temperature, evaporated to dryness, then dissolved in dimethylformamide (50 ml) containing methanolic sodium methoxide (1 ml from 0.06 g sodium). The solution was stirred for one hour at 85°–95°, evaporated in vacuo, diluted with water and the product either removed by filtration or extracted into chloroform. Melting-points are shown in Table 1.

Certain examples (e.g. Compound Nos. 8 and 9) give mixtures of endo- and exo-alkylated products under standard conditions but further isomerization to the desired exoisomer can be achieved by more vigorous methoxide treatment. In other cases (e.g. Compound No. 1), the alkoxide treatment can be omitted.

EXAMPLE 2

This Example illustrates the preparation of Compound nos 5, 17, 40, 172 and 177 of Table I.

A mixture of 2-amino-3-cyanothiophene (30 g) and a triethylorthoester (90 ml) was heated on a steam bath for 90 minutes, evaporated and distilled to give the 2-ethoxymethyleneamino-3-cyanothiophene (e.g. 2-H, 37.4 g, m.p. 38°, b.p. 104°–9°/0.05 mm; 2-CH$_3$, 40.0 g, b.p. 78°–82°/0.01 mm). The appropriate product was treated with an amine or hydrazine (see Example 7), anhydrous sodium acetate and acetic acid and the mixture heated (90°–150°) until reaction complete (e.g. 30 minutes to 48 hours). The mixture was cooled, diluted with water and the product either removed by filtration or extracted into a solvent (e.g. ether). Following recrystallisation from a suitable solvent, the products had melting-points as shown in Table 1.

EXAMPLE 3

This Example illustrates the preparation of Compound No. 243 of Table 1.

Examples 1 and 2 could not be made to operate where the variable amine also contained an acid function e.g. an amino-acid. The following modification was successful.

A mixture of DL-alanine (9.0 g), 2-ethoxymethyleneamino-3-cyanothiophene (4.0 g, prepared as described in Example 2) and 5N sodium hydroxide solution was heated to 45°, then allowed to cool slowly for 30 minutes. It was then cooled to 0° and the precipitate filtered off and treated with a further quantity of 5N sodium hydroxide solution (12 ml) at 100° for 8 minutes. The mixture was cooled, acidified to pH 5 with dilute hydrochloric acid and the precipitate filtered off, washed with a little water and recrystallised from aqueous ethanol to give the title compound (1.03 g, m.p. 175°).

EXAMPLE 4

This Example illustrates the preparation of 4-isopropylaminothieno[2,3-d]pyrimidine (Compound No. 5) by an alternative procedure to that described in Examples 1 and 2.

A mixture of sodium hydride (0.64 g, 100%), 4-aminothieno[2,3-d]pyrimidine (3.5 g) and dry dimethylformamide (25 ml) was stirred for fifteen minutes at <20°, then treated with 2-iodopropane (3.5 ml). After stirring at <20° for ninety minutes, the reaction mixture was diluted with water and cooled in ice. The precipitate was washed with water, dried and recrystallised from acetonitrile to give the title compound (1.4 g, m.p. 225°–6°).

EXAMPLE 5

This Example illustrates the preparation of a number of 4-aminothieno[2,3-d]pyrimidines by an alternative procedure to those described in Examples 1, 2 and 4. By this procedure compounds nos. 1–3, 5, 12 and 16–128, 172–175, 178–185, 188–190, 192, 194–200, 202–203, 205–208, 212, 214, 217–218, 223–224, 227–234, 237–240, 244–249, were prepared.

A mixture of an appropriately substituted 4-chlorothieno[2,3-d]pyrimidine and either a primary or secondary amine*, neat or together with a solvent (e.g. a lower alcohol, particularly ethanol), was allowed to react for one-half to twenty hours at 20° C. to 160° C. depending on the nature of the reagents. It was then diluted with water** and the product either removed by filtration or extracted into chloroform. Melting-points (after recrystallisation, or reprecipitation from acid) or boiling-points (bulb-tube distillation, bath temperature; shown in brackets) are shown in Table 1.

*The amine must either be used in excess (>2 equivalents) or in the presence of at least one equivalent of a base e.g. triethylamine. Where the amine was available only as a hydrochloride, the mixture comprised the chloro compound (1 equivalent), amine hydrochloride (2 equivalents), 10N aqueous sodium hydroxide solution (2 equivalents) and ethanol.

**In some cases, neutralisation with carbon dioxide at this stage is preferable.

EXAMPLE 6

This Example illustrates the preparation of several 4-hydrazinothieno[2,3-d]pyrimidines according to the invention (Compound Nos. 129–133 and 225, Table 1).

The appropriate 4-chloro derivative was treated with hydrazine or a monosubstituted derivative thereof, basically as described for amines in Example 5. Whilst only one product can be obtained in the case of hydrazine itself, substituted hydrazines could react on either nitrogen atom. In practice, reaction only at the more substituted position is observed. Melting-points are given in Table 1.

1,1-Disubstituted hydrazines react abnormally under these conditions. Thus, following reaction at the more substituted nitrogen atom, loss of either an alkyl group (1,1-dimethylhydrazine giving Compound No. 130) or an amino group (1-methyl-1-phenylhydrazine giving Compound No. 50) can occur. Alternative conditions leading to products containing the NHNR$_2$ moiety are described in Example 7.

EXAMPLE 7

This Example describes the preparation of several hydrazinium chlorides (Compound Nos. 176 and 187) and their rearrangement to hydrazines (Compound Nos. 177 and 191).

4-Chlorothieno[2,3-d]pyrimidine (10 g) was added to an ice-cooled mixture of 1,1-dimethylhydrazine (9 ml) and acetonitrile (150 ml). The reaction mixture was allowed to stir at room temperature for 2½ hours, and the precipitate filtered off, washed with acetonitrile and ether. The product (11.7 g, m.p. 124°) is Compound No. 176 of Table 1. Compound No. 187 was made similarly from 1-aminopiperidine.

A mixture of Compound No. 176 (5.0 g, prepared as described above), 1,5-diazabicyclo[4.3.0]non-5-ene (6 g) and acetonitrile (50 ml) was refluxed for one hour, evaporated and the residue partitioned between chloroform and ammonium chloride solution. The chloroform layer was washed, dried and evaporated and the residue washed with petrol, then recrystallised from acetonitrile to give Compound No. 177 (2.48 g, m.p. 157°). Compound No. 191 was prepared likewise from Compound No. 187.

Compound No. 177 can also be prepared by the method described in Example 2, using 1,1-dimethylhydrazine in place of the amine.

EXAMPLE 8

This example illustrates the preparation of several 4-amino-6-nitrothieno[2,3-d]pyrimidines according to the invention (Compounds Nos. 134 and 135 of Table 1).

A mixture of 4-isopropylaminothieno[2,3-d]pyrimidine (4.0 g, prepared as described in Example 5) and concentrated sulphuric acid (20 ml) was cooled to 0° and treated dropwise with a mixture of concentrated nitric acid (2.2 ml) and concentrated sulphuric acid (2.0 ml) whilst maintaining the temperature below 12° C. The mixture was allowed to stir at room temperature for a further one hour, poured into icewater and neutralised with sodium carbonate. The precipitate was filtered off, washed with water and dried to give 4-isopropylamino-6-nitrothieno[2,3-d]pyrimidine (4.58 g, m.p. 200°) (Compound No. 134).

4-Diethylaminothieno[2,3-d]pyrimidine (2 g) was nitrated similarly to give the 6-nitro derivative (2.34 g, m.p. 135°) (Compound No. 135).

EXAMPLE 9

This Example illustrates the preparation of several 4-amino-6-nitrothieno[2,3-d]pyrimidines by an alternative procedure to that described in Example 8.

A mixture of 3,4-dihydrothieno[2,3-d]pyrimidin-4-one (21 g) and concentrated sulphuric acid (140 ml) was treated with mixture of concentrated nitric acid (15.4 ml) and concentrated sulphuric acid (14 ml) maintaining the temperature below 10° C. The mixture was stirred for a further hour at room temperature, poured into ice/water and the precipitate filtered off, washed with water and dried to give the 6-nitro derivative (24.6 g, m.p. 307°). A mixture of this material (15 g) and phosphorus oxychloride (200 ml) was refluxed for three hours, the excess reagent removed in vacuo and the residue treated with chloroform (400 ml) and ice-water (400 ml). The organic layer was washed with brine, dried and evaporated to give 4-chloro-6-nitrothieno[2,3-d]pyrimidine (16.9 g, m.p. 112°). Recrystallisation from acetonitrile gave material, m.p. 116°–118°.

Treatment of this chloro compound with amines (basically as described in Example 5) gave, for example, the 4-isopropylamino (m.p. 199°, Compound No. 134), and 4-benzylamino (m.p. 214°, Compound No. 136) derivatives.

EXAMPLE 10

This Example illustrates the preparation of 4-amino-6-nitrothieno[2,3-d]pyrimidines by an alternative procedure to that described in Examples 8 or 9.

Phosphorus oxychloride (5 ml) was added dropwise, with stirring, to dry N,N-dimethylformamide (20 ml) maintaining the temperature below 5° C. The solution was allowed to stand for fifteen minutes then treated, at 0°–5° C., with a suspension of 2-amino-3-cyano-5-nitrothiophene (5.1 g) in dry N,N-dimethylformamide (50 ml), allowed to attain room temperature, then kept at 20° C. for five days. It was then poured on to ice, the precipitate removed and the filtrate basified with ammonium hydroxide solution to give 2-dimethylaminomethyleneamino-3-cyano-5-nitrothiophene (m.p. 230°). A mixture of this material (0.5 g), benzylamine (0.26 g) and ethanol (100 ml) was refluxed for twelve hours, treated with acetic acid (0.5 ml) and heating continued for a further thirty minutes. The solvent was removed in vacuo and the residue diluted with water to give 4-benzylamino-6-nitrothieno[2,3-d]pyrimidine (0.4 g) (Compound No. 136).

EXAMPLE 11

This Example describes the preparation of 6-acetylamino-4-isopropylaminothieno[2,3-d]pyrimidine having the structural formula:

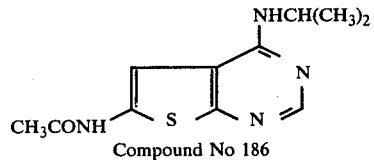

Compound No 186

A mixture of Compound No. 134 (3.0 g, prepared as described in Example 8), activated iron powder (4.8 g, prepared from zinc and ferrous sulphate), acetic anhydride (12 ml) and acetic acid (60 ml) was heated at 85° for 4 hours, cooled and poured into water. The precipitate was filtered off, dried and recrystallised from acetonitrile to give the title compound (1.37 g, m.p. 319°).

EXAMPLE 12

This Example illustrates the preparation of several 4-amino-2-chlorothieno[2,3-d]pyrimidines according to the invention. By this procedure Compound Nos. 137 to 144, 193, 201 and 204 of Table 1 were prepared.

A mixture of 2-amino-3-carbonamidothiophene (100 g), sodium carbonate (106 g), ethyl chloroformate (140 ml) and ethanol (1.5 l) was heated at 40° for twenty minutes, filtered and poured into water (5 l) to give, after drying, 3-carbonamido-3-ethoxycarbonylaminothiophene (48.3 g, m.p. 195°). This material (45 g) was suspended in a solution of sodium carbonate (90 g) in water (900 ml), heated for two hours at 100°, cooled and acidified with hydrochloric acid to give 1,2,3,4-tetrahydrothieno[2,3-d]pyrimidin-2,4-dione (30 g, m.p. >300°). This material (45.0 g) was added slowly to phosphorus oxychloride (320 ml), followed by pyridine (45 ml), and the mixture refluxed for one hour. Excess phosphorus oxychloride was removed in vacuo, the residue poured, with stirring, into ice-water then extracted with chloroform. The extracts were evaporated to give 2,4-dichlorothieno[2,3-d]pyrimidine (34.2 g). After recrystallisation from petroleum (b.p. 80°-100° C.), this had m.p. 116°.

A mixture of this material and excess primary or secondary amine, either neat or together with a solvent, was allowed to react at room temperature for ten minutes. It was then diluted with water* and the product either removed by filtration or extracted with chloroform. Melting-points, after recrystallisation from a suitable solvent, are shown in Table 1.

*In some cases, neutralisation with carbon dioxide at this state is preferable.

EXAMPLE 13

This Example illustrates the preparation of several 2-substituted-4-aminothieno[2,3-d]pyrimidine according to the invention. By this procedure compounds nos. 145-164 and No. 254 of Table 1 were prepared.

The appropriate 2-chloro-4-aminothieno[2,3-d]pyrimidine, prepared as described in Example 12, was treated with the appropriate reagent(s) as shown in Table 2 to give the required derivative.

TABLE 2

| COMPOUND NO. (OF TABLE 1) | REACTION CONDITIONS (FROM COMPOUND NO. 137) OF TABLE 1 UNLESS OTHERWISE STATED) |
|---|---|
| 145 | imidazole, fusion, 100° |
| 146 | 1,2,4-triazole, fusion, 160° |
| 147 | NaOCH$_3$, methanol, reflux |
| 148 | hydrazine hydrate, ethanol, reflux |
| 149 | morpholine, reflux |
| 150 | pyrazole, fusion, 150° |
| 151 | Compound No. 148 + acetylacetone |
| 152 | Compound No. 148 + nitrous acid |
| 153 | NaSCH$_3$, N,N-dimethylformamide |
| 154 | piperidine, reflux |
| 155 | Compound No. 153, two equivalents 3-chloroperbenzoic acid, chloroform |
| 156 | pyrrolidine, reflux |
| 157 | Compound No. 153, one equivalent 3-chloroperbenzoic acid chloroform |
| 158 | isobutylamine, reflux |
| 159 | sodium cyanide, dimethylsulphoxide, 140° |
| 160 | concentrated hydrochloric acid, reflux |
| 161 | Compound No. 143, concentrated hydrochloric acid, reflux |

TABLE 2-continued

| COMPOUND NO. (OF TABLE 1) | REACTION CONDITIONS (FROM COMPOUND NO. 137) OF TABLE 1 UNLESS OTHERWISE STATED) |
|---|---|
| 162 | Compound No, 159, 5N sodium hydroxide, ethanol, reflux |
| 163 | thiourea, hydrochloric acid, then sodium hydroxide solution |
| 164 | Compound No. 144, isobutylamine, reflux |
| 254 | 2-mercaptoacetamide, potassium carbonate, ethanol, reflux |

EXAMPLE 14

This Example illustrates the preparation of 4-acetylaminothieno[2,3-d]pyrimidine having the structural formula:

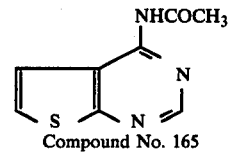

Compound No. 165

A mixture of 4-aminothieno[2,3-d]pyrimidine (7.55 g prepared as described in Example 1) and acetic anhydride (10 ml) was refluxed for 6 hours and evaporated in vacuo. The residue was recrystallised from ethanol to give the title compound (6.61 g, m.p. 189°-191°).

EXAMPLE 15

This Example illustrates the preparation of 4-diacetylaminothieno[2,3-d]pyrimidine having the structural formula:

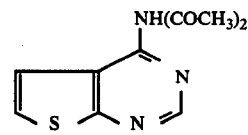

A mixture of 4-aminothieno[2,3-d]pyrimidine (4.53 g, prepared as described in Example 1), acetic anhydride (25 ml) and pyridine (50 ml) was refluxed for eighteen hours and evaporated to dryness. The residue was extracted with boiling cyclohexane (3×100 ml) and the extracts treated with charcoal, then filtered and cooled to give the title compound (2.04 g, 102°-104°).

EXAMPLE 16

This Example illustrates the preparation of several 4-acetylaminothieno[2,3-d]pyrimidines according to the invention. By this procedure compounds Nos. 167 and 168 were prepared.

A mixture of 4-isopropylaminothieno[2,3-d]pyrimidine (prepared as described in Example 5, 3.2 g), acetic anhydride (12 ml) and pyridine (25 ml) was refluxed for twenty-four hours, then evaporated to dryness. The residue was extracted with boiling cyclohexane and the extracts treated with charcoal, filtered and cooled to give the 4-acetylisopropylamino derivative (1.8 g, m.p. 81-84; Compound No. 167). The n-propylamino analogue, made similarly, had m.p. 48°-53°; (Compound No. 168).

EXAMPLE 17

This Example illustrates the preparation of 4-acetylisobutylaminothieno[2,3-d]pyrimidin-2-one, Compound No. 169, having the structural formula:

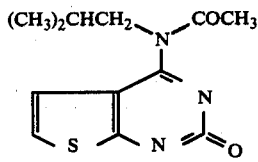

A mixture of 4-isobutylaminothieno[2,3-d]pyrimidin-2-one (Compound No. 161, prepared as described in Example No. 13, 3.5 g) and acetic anhydride (25 ml) was refluxed for eight hours and the excess reagent removed in vacuo. The residue was chromatographed on silica gel (dry column technique, ether) to give the 4-acetylisobutylamino-2-acetoxy derivative (1.3 g, m.p. 88°). This material (880 mg) was treated with a solution of sodium methoxide (from 100 mg of sodium) in methanol (20 ml) and allowed to stand for three days. The solvent was removed in vacuo and the residue treated with dilute hydrochloric acid. Extraction with chloroform gave the title compound (500 mg, m.p. 147°, Compound No. 169).

EXAMPLE 18

This Example illustrates the preparation of a number of salts of several 4-aminothieno[2,3-d]pyrimidines, having Compound Nos. 170, 171, 209–211, 213, 215–6, 219–222 and 226.

A mixture of the appropriate 4-amino derivative and excess organic or inorganic acid, either neat or in aqueous solution, was stirred, with heating if necessary, to give a homogeneous solution. The product was obtained either by cooling and filtration or evaporation to dryness. Melting-points, following recrystallisation are shown in Table 1.

EXAMPLE 19

This Example illustrates the preparation of several 4-amino-6-bromo-thieno[2,3-d]pyrimidines according to the invention (Compound Nos. 235–6, 241–2).

A mixture of 3,4-dihydrothieno[2,3-d]pyrimidine-4-one (21 g), bromine (30 ml) and acetic acid (300 ml) was stirred at room temperature for three hours, poured into water/ice (1 l) and the 6-bromo derivative filtered off and dried (18.2 g). A portion (17.0 g) was treated with thionyl chloride (230 ml) and N,N-dimethylformamide (3 ml) and refluxed for forty minutes. Excess acid chloride was removed in vacuo and the residue was partitioned between chloroform and water. The organic layer was washed, dried and evaporated to give 6-bromo-4-chlorothieno[2,3-d]pyrimidine (14.7 g). This was treated with a number of amines basically as described in Example 5.

EXAMPLE 20

This Example illustrates the preparation of several 4-amino-6-dimethylsulphonamidothieno[2,3-d]pyrimidines according to the invention (Compound Nos. 250–253).

3,4-Dihydrothieno[2,3-d]pyrimidin-4-one (50 g) was added portionwise to chlorosulphonic acid (243 ml), maintaining the temperature below 0° C. Thionyl chloride (121 ml) was added dropwise, and the mixture stirred for a further 30 minutes at room temperature; then two hours at reflux. It was then cooled, and poured carefully on to ice. The precipitate was washed and dried to give 6-chlorosulphonylthieno[2,3-d]pyrimidin-4-one (84 g). This compound (30 g) and dimethylamine (450 ml) were mixed at −10°, then allowed to stir at room temperature for two hours. The mixture was poured into water and acidified with hydrochloric acid. The precipitate was washed with water and ethanol, and dried to give the 6-dimethylsulphonamido-4-one (23.8 g). This material was converted into the 4-chloro derivative as described in Example 19 above and thence into the title compounds by treatment with amines basically as described in Example 5.

EXAMPLE 21

An emulsifiable concentrate was made up by mixing together the ingredients set out below in the proportions stated and stirring the mixture until all the constituents were dissolved.

| Compound No. 5 of Table 1 | 10% |
|---|---|
| Ethylene Dichloride | 40% |
| Calcium dodecylbenzenesulphonate | 5% |
| "Lubrol" L | 10% |
| "Aromasol" H | 35% |

EXAMPLE 22

A composition in the form of grains readily dispersible in a liquid, e.g. water, was prepared by grinding together the first three of the ingredients listed below in the presence of added water and then mixing in the sodium acetate. The resultant mixture was dried and passed through a British Standard mesh sieve, size 44–100, to obtain the desired size of grains.

| Compound No. 7 of Table 1 | 50% |
|---|---|
| "Dispersol" T | 25% |
| "Lubrol" APN 5 | 1.5% |
| Sodium Acetate | 23.5% |

EXAMPLE 23

The ingredients listed below were all ground together in the proportions stated to produce a powder formulation readily dispersible in liquids.

| Compound No. 8 of Table 1 | 45% |
|---|---|
| "Dispersol" T | 5% |
| "Lissapol" NX | 0.5% |
| "Cellofas" B600 | 2% |
| Sodium acetate | 47.5% |

EXAMPLE 24

The active ingredient (Compound No. 9 of Table 1) was dissolved in a solvent and the resultant liquid was sprayed on to the granules of Fuller's earth. The solvent was then allowed to evaporate to produce a granular composition.

| Compound No. 9 of Table 1 | 5% |
|---|---|
| Fuller's earth of China clay granules | 95% |

EXAMPLE 25

A dusting powder was prepared by mixing, in the proportions stated, the active ingredient with talc.

| | |
|---|---|
| Compound No. 30 of Table 1 | 5% |
| Talc | 95% |

EXAMPLE 26

A Col formulation was prepared by ball-milling the constituents set out below and then forming an aqueous suspension of the ground mixture with water.

| | |
|---|---|
| Compound No. 40 of Table 1 | 40% |
| "Dispersol" T | 10% |
| "Lubrol" APN5 | 1% |
| Water | 49% |

EXAMPLE 27

A dispersible powder formulation was made by mixing together the ingredients set out below and then grinding the mixture until all the constituents were thoroughly mixed.

| | |
|---|---|
| Compound No. 7 of Table 1 | 25% |
| "Aerosol" OT/B | 2% |
| "Dispersol" A.C. | 5% |
| China Clay | 28% |
| Silica | 40% |

EXAMPLE 28

This example illustrates the preparation of a dispersible powder formulation. In each instance all the ingredients are mixed in the proportions stated and the mixture then ground in a comminution mill.

| | |
|---|---|
| Compound No. 109 of Table 1 | 25% |
| "PERMINAL" BX | 1% |
| "Dispersol" T | 5% |
| Polyvinylpyrrolidone | 10% |
| Silica | 25% |
| China Clay | 34% |

EXAMPLE 29

The ingredients set out below were formulated into a dispersible powder by mixing and grinding the ingredients in the proportions stated.

| | |
|---|---|
| Compound No. 119 of Table 1 | 25% |
| "AEROSOL" OT/B | 2% |
| "Dispersol" A | 5% |
| China Clay | 68% |

Exactly the same formulations as set out in Examples 21 to 29 were prepared using the remaining Compounds of Table I.

In Examples 21 to 29 above percentage amounts are on a weight basis.

The following constitutes an explanation of the compositions or substances represented by the virious Trade Marks and Trade Names referred to in the foregoing Examples.

"LUBROL" L is a condensate of 1 mole of nonyl phenol with 13 molar proportions of ethylene oxide.

"AROMASOL" H is a solvent mixture of alkylbenzenes.

"DISPERSOL" T AND AC is a mixture of sodium sulphate and a condensate of formaldehyde with the sodium salt of naphthalene sulphonic acid.

"LUBROL" APN 5 is a condensate of 1 mole of nonyl phenol with 5½ moles of naphthalene oxide.

"CELLOFAS" B 600 is a sodium carboxymethyl cellulose thickener.

"LISSAPOL" NX is a condensate of 1 mole of nonyl phenol with 8 moles of ethylene oxide.

"AEROSOL" OT/B is dioctyl sodium sulphosuccinate.

"PERMINAL" BX is an alkyl naphthalene sulphonate (sodium salt).

EXAMPLE 30

The compounds and compositions of the invention were tested against a variety of foliar fungal disease of plants. The technique employed is to spray the foliage of the plants to maximum retention with a solution or suspension of the test compound and also to apply the same to the roots of the plant via the soil to a final concentration equivalent, approximately, to 40 p.p.m. of the compound in the dry soil. Spray formulations onto cereals contain 0.1% of a surface active agent.

All solutions or suspensions for spraying and application to the soil contained 100 parts per million (p.p.m.) of the test compound, and the plants were grown in potting compost in pots of 4 cm diameter.

The plants were infected with the disease it was desired to control before or after application of the chemical and after a period of days, depending upon the particular disease, the extent of the disease was visually assessed.

The results are given in the Table below, in the form of a grading as follows:

| Grading | Percentage Amount of Disease |
|---|---|
| 0 | 61 to 100 |
| 1 | 26 to 60 |
| 2 | 6 to 25 |
| 3 | 0 to 5 |
| 4 | 0 |

In Table 3 below, the disease is given in the first column, whilst in the second column is given the time which elapsed between infecting the plants and assessing the amount of disease. The third column assigns to each disease a code letter, these code letters being used in Table 4 to identify the diseases.

TABLE 3

| DISEASE AND PLANT | TIME INTERVAL (DAYS) | DISEASE CODE LETTER (TABLE NO. 4) |
|---|---|---|
| (1) Puccinia recondita (wheat) | 10 | A |
| (2) Phytophthora infestans (tomato) | 3 | B |
| (3) Plasmopara viticola (vine) | 7 | C |
| (4) Piricularia oryzae (rice) | 7 | D |
| (5) Botrytis cinerea | 3 | E |

TABLE 3-continued

| DISEASE AND PLANT | TIME INTERVAL (DAYS) | DISEASE CODE LETTER (TABLE NO. 4) |
|---|---|---|
| (tomato) | | |
| (6) Erysiphe graminis (barley) | 7 | F |

TABLE 4

| COMPOUND NO. | A | B | C | D | E | F |
|---|---|---|---|---|---|---|
| 1 | 2 | 0 | 0 | 0 | — | 0 |
| 2 | 1 | 1 | 1 | 0 | 3 | 1 |
| 3 | 0 | 4 | 0 | 0 | — | 1 |
| 4 | 2 | 3 | 0 | 2 | — | 4 |
| 5 | 4 | 4 | — | 3 | 0 | 4 |
| 6 | 1 | 3 | — | 0 | 2–3 | 3 |
| 7 | 4 | 0 | 3 | 2 | — | 2 |
| 8 | 0 | 4 | 2–3 | 1 | 0 | 1 |
| 9 | 3 | 0 | 3 | 0 | 0 | 2 |
| 10 | 0 | 3 | 3 | 2 | 0 | 0 |
| 11 | 3 | 3 | 3 | — | 0 | 3 |
| 12 | 1 | 4 | 3 | — | 0 | 0 |
| 13 | 1 | 2 | 2 | 0 | 0 | 1 |
| 14 | 0 | 1 | 3 | 1 | 0 | 0 |
| 15 | 1 | 1 | 0 | 3 | 1 | 1 |
| 16 | 0 | 4 | 2 | — | 2 | 2 |
| 17 | 2 | 4 | 4 | — | 1 | 0 |
| 18 | 4 | 2 | 3 | 1 | 4 | 2 |
| 19 | 0 | 0 | — | 2 | 1 | 1 |
| 20 | 3 | 3 | — | 3 | 2 | 3 |
| 21 | 3 | 4 | — | 3 | 1 | 2 |
| 22 | 1 | 0 | 0 | 1 | 0 | 1 |
| 23 | 4 | 3 | — | 3 | 2 | 4 |
| 24 | 4 | 3 | 0 | 3 | 2 | 4 |
| 25 | 1 | 4 | — | — | — | — |
| 26 | 1 | 2 | — | — | — | — |
| 27 | 4 | 3 | 1 | 2 | — | 1 |
| 28 | 2 | 4 | — | 0 | — | — |
| 29 | 2 | 2 | 3 | 0 | 1 | 2 |
| 30 | 4 | 4 | 3 | 1 | 0 | 3 |
| 31 | 1 | 3 | 0 | 0 | 2 | 0 |
| 32 | 4 | 4 | 0 | — | 0 | 3 |
| 33 | 3 | 4 | 3 | — | 0 | 3 |
| 34 | 2 | 3 | 1 | 0 | 0 | 0 |
| 35 | 3 | 4 | 3 | 0 | 1 | 3 |
| 36 | 3 | 4 | 3 | 0 | 2 | 2 |
| 37 | 1 | 0 | 0 | 0 | 0 | 0 |
| 38 | 0 | 2 | 0 | 0 | 0 | 0 |
| 39 | 0 | 2 | 0 | 0 | 0 | 0 |
| 40 | 4 | 4 | 0 | 3 | 0 | 4 |
| 41 | 2 | 4 | 3 | 3 | 0 | 0 |
| 42 | 1 | 3 | 2 | 3 | 2 | 1 |
| 43 | 1 | 1 | 4 | 1 | 2 | 2 |
| 44 | 3 | 4 | 4 | 3 | 1 | 0 |
| 45 | 1 | 1 | 4 | 2 | 1 | 1 |
| 46 | 2 | 4 | 4 | 1 | 1 | 0 |
| 47 | 3 | 4 | 4 | 2 | 1 | 3 |
| 48 | 1 | 1 | 3 | 1 | 2 | 0 |
| 49 | 2 | 4 | 4 | 1 | 0 | 1 |
| 50 | 1 | 3 | 4 | 3 | 0 | 0 |
| 51 | 1 | 4 | 2 | 3 | 0 | 0 |
| 52 | 0 | 1 | 0 | 0 | 0 | 1 |
| 53 | 0 | 3 | 0 | 2 | 0 | 2 |
| 54 | 1 | 4 | 4 | 2 | 0 | 0 |
| 55 | 1 | 0 | 0 | 0 | 0 | 3 |
| 56 | 3 | 4 | 3 | 3 | 3 | 3 |
| 57 | 2 | 0 | 2 | 3 | 3 | 3 |
| 58 | 2 | 0 | 1 | 2 | 2 | 2 |
| 59 | 1 | 4 | 0 | — | 1 | 1 |
| 60 | 2 | 0 | 0 | 2 | 0 | 2 |
| 61 | 3 | 2 | 0 | 1 | 0 | 0 |
| 62 | 3 | 3 | 0 | — | 0 | 2 |
| 63 | 3 | 2 | 0 | — | 0 | 1 |
| 64 | 1 | 0 | 0 | 0 | 0 | 0 |
| 65 | 0 | 1 | — | 1 | 2 | 0 |
| 66 | 2 | 4 | 3 | 3 | 2 | — |
| 67 | 2 | 4 | 2 | 2 | 2 | 0 |
| 68 | 0 | 2 | 3 | 2 | 3 | 0 |
| 69 | 1 | 4 | 0 | 2 | 1 | 0 |
| 70 | 0 | 0 | 0 | 3 | 0 | — |
| 71 | 2 | — | — | 1 | 3 | 0 |
| 72 | 3 | 1 | 0 | 1 | 3 | 3 |
| 73 | 3 | 4 | 3 | 1 | 3 | 2 |
| 74 | 3 | 2 | 1 | 2 | 4 | 2 |
| 75 | 0 | 4 | 0 | 2 | 2 | 2 |
| 76 | 1 | 4 | 0 | 0 | 3 | 0 |
| 77 | 1 | 0 | 0 | 1 | 2 | 0 |
| 78 | 3 | 4 | 0 | 0 | 1 | 0 |
| 79 | 4 | 4 | 3 | 1 | 0 | 3 |
| 80 | 0 | 0 | 0 | 0 | 2 | 0 |
| 81 | 3 | 0 | 3 | 2 | 2 | 2 |
| 82 | 2 | 3 | 0 | 1 | 0 | 2 |
| 83 | 2 | 2 | 0 | 2 | 0 | 3 |
| 84 | 1 | 1 | 0 | 2 | 0 | 3 |
| 85 | 0 | 3 | 0 | 2 | 0 | 1 |
| 86 | 0 | 0 | 0 | 1 | 0 | 0 |
| 87 | 3 | 3 | 0 | 3 | 0 | 4 |
| 88 | 2 | 4 | 0 | 3 | 1 | 3 |
| 89 | 3 | 4 | 2 | 1 | 0 | 3 |
| 90 | 0 | 0 | 0 | 1 | 0 | 0 |
| 91 | 3 | 0 | 0 | 2 | 0 | 3 |
| 92 | 0 | 4 | 0 | 0 | 0 | 2 |
| 93 | 2 | 4 | 0 | — | 0 | 3 |
| 94 | 0 | 3 | 0 | 0 | 2 | 3 |
| 95 | 0 | 4 | 3 | 2 | 0 | 0 |
| 96 | 1 | 0 | 0 | 2 | 0 | 0 |
| 97 | 0 | 0 | 0 | 2 | 0 | 0 |
| 98 | 0 | 0 | 2 | 0 | 0 | 0 |
| 99 | 0 | 0 | 1 | 0 | 0 | 0 |
| 100 | 0 | 2 | 1 | 0 | 0 | 2 |
| 101 | 0 | 3 | 1 | 0 | 0 | 2 |
| 102 | 4 | 4 | 3 | 0 | 2 | 3 |
| 103 | 1 | 3 | 0 | 0 | 0 | 0 |
| 104 | — | 0 | 0 | 0 | 2 | 0 |
| 105 | 1 | 3 | 2 | 1 | 0 | 0 |
| 106 | 1 | 0 | 0 | 3 | 0 | 0 |
| 107 | 3 | 4 | 3 | 3 | 0 | 3 |
| 108 | 3 | 4 | 1 | 0 | 0 | 1 |
| 109 | 3 | 4 | 1 | 0 | 0 | 1 |
| 110 | 2 | 0 | 0 | 0 | 0 | 0 |
| 111 | 1 | 2 | 1 | 2 | 0 | 0 |
| 112 | 2 | 0 | 0 | 1 | 2 | 1 |
| 113 | 0 | 2 | 0 | — | 0 | 0 |
| 114 | 0 | 1 | 0 | 0 | 0 | 0 |
| 115 | 0 | 2 | 0 | 0 | 0 | 0 |
| 116 | 3 | 4 | 0 | 0 | 0 | 3 |
| 117 | 3 | 4 | 3 | — | 0 | 3 |
| 118 | 3 | 2 | 2 | 1 | 3 | 4 |
| 119 | 4 | 4 | 0 | 1 | 0 | 4 |
| 120 | 0 | 0 | 0 | 0 | 0 | 2 |
| 121 | 2 | 3 | 0 | 1 | 0 | 2 |
| 122 | 1 | 4 | 0 | 2 | 0 | 0 |
| 123 | 0 | 0 | 0 | 1 | 0 | 0 |
| 124 | 0 | 3 | 0 | 0 | 2 | 3 |
| 125 | 1 | 0 | 0 | 1 | 0 | 0 |
| 126 | 0 | 3 | 0 | 0 | 0 | 0 |
| 127 | 1 | 1 | 0 | 0 | 0 | 1 |
| 128 | 1 | 2 | 2 | 2 | 0 | 1 |
| 129 | 1 | 3 | 0 | 0 | 0 | 0 |
| 130 | 1 | 1 | 0 | 1 | 0 | 0 |
| 131 | 0 | 1 | 3 | 3 | 1 | 0 |
| 132 | 0 | 0 | 3 | 1 | 0 | 0 |
| 133 | 0 | 1 | 3 | 0 | 2 | 0 |
| 134 | 2 | 0 | 0 | 3 | 0 | 1 |
| 135 | 1 | 1 | 0 | 1 | 2 | 0 |
| 136 | 1 | 1 | 0 | 1 | 3 | 2 |
| 137 | 1 | 4 | — | 3 | 0 | — |
| 138 | 2 | 3 | — | — | — | — |
| 139 | — | 2 | — | 0 | 0 | 2 |
| 140 | 0 | 2 | 0 | 0 | 2 | 0 |
| 141 | 2 | 3 | 3 | 0 | 2 | 0 |
| 142 | 1 | 2 | 0 | 2 | 2 | 1 |
| 143 | 2 | 4 | 3 | 3 | 1 | 0 |
| 144 | 0 | 0 | 0 | 0 | 1 | — |
| 145 | 1 | 1 | 0 | 0 | 1 | 0 |
| 146 | 2 | 2 | 0 | 0 | 0 | 1 |
| 147 | 0 | 3 | 0 | 1 | 0 | 1 |
| 148 | 4 | 4 | 0 | 3 | 2 | 1 |
| 149 | 2 | 2 | 0 | 3 | 2 | 1 |
| 150 | 1 | 0 | 3 | 1 | 0 | 0 |
| 151 | 1 | 1 | 0 | 1 | 0 | 2 |
| 152 | 1 | 4 | 4 | 1 | 3 | 0 |
| 153 | 0 | 2 | 0 | 2 | 0 | 0 |
| 154 | 0 | 3 | 0 | — | 0 | 2 |
| 155 | 0 | 3 | 0 | — | 0 | 0 |
| 156 | 1 | 0 | 0 | — | 0 | 0 |
| 157 | 0 | 3 | 2 | 1 | 0 | — |
| 158 | 1 | 4 | 3 | 1 | 1 | 0 |
| 159 | 1 | 2 | 0 | 0 | 1 | 1 |
| 160 | 0 | 0 | 0 | 3 | 0 | 0 |
| 161 | 0 | 0 | 0 | 1 | 0 | 0 |
| 162 | 0 | 1 | 0 | 0 | 0 | 0 |
| 163 | 0 | 0 | 3 | 3 | 0 | 0 |
| 164 | 0 | 2 | 0 | 0 | 1 | 0 |
| 165 | 0 | 0 | — | 1 | 0 | 0 |
| 166 | 0 | 4 | 3 | 0 | 0 | 0 |
| 167 | 2 | 3 | 0 | 0 | 0 | 1 |
| 168 | 1 | 3 | 0 | 1 | 0 | 2 |
| 169 | 0 | 0 | 1 | 3 | 2 | 2 |
| 170 | 4 | 4 | 0 | 3 | 2 | 2 |

TABLE 4-continued

| COMPOUND NO. | A | B | C | D | E | F |
|---|---|---|---|---|---|---|
| 171 | 0 | 0 | 0 | 1 | 1 | 0 |
| 172 | 3 | 3 | 4 | 1 | 1 | 3 |
| 173 | 3 | 4 | 0 | 2 | 0 | 0 |
| 174 | 3 | 3 | 3 | 1 | 2 | 3 |
| 175 | 3 | 4 | 0 | 2 | 2 | 3 |
| 176 | — | 0 | 3 | 1 | 3 | 1 |
| 177 | — | 3 | 0 | 4 | 2 | 1 |
| 178 | — | 3 | 3 | 3 | 2 | 2 |
| 179 | — | 4 | 3 | 2 | 3 | 3 |
| 180 | 3 | 1 | 0 | 0 | 3 | 4 |
| 181 | 3 | 3 | 1 | 2 | 2 | 4 |
| 182 | 1 | 3 | 0 | 0 | 0 | 0 |
| 183 | 3 | 1 | 2 | 3 | 0 | 2 |
| 184 | 0 | 2 | 1 | 0 | 0 | 0 |
| 185 | 3 | 4 | 3 | 2 | 0 | 3 |
| 186 | 0 | 1 | 1 | 0 | 0 | 0 |
| 187 | 0 | 0 | 0 | 3 | 0 | 1 |
| 188 | 0 | 2 | 0 | 0 | 0 | 0 |
| 189 | 3 | 4 | 2 | 0 | 0 | 3 |
| 190 | 0 | 0 | 0 | 2 | 0 | 0 |
| 191 | 0 | 0 | 0 | 1 | 0 | 0 |
| 192 | 0 | 0 | 0 | 0 | 1 | 0 |
| 193 | 0 | 4 | 3 | 2 | 0 | 0 |
| 194 | 0 | 0 | 0 | 1 | 0 | 0 |
| 195 | 0 | 0 | 3 | 0 | 0 | 0 |
| 196 | 0 | 0 | 0 | 2 | 0 | 0 |
| 197 | 0 | 0 | 0 | 2 | 0 | 0 |
| 198 | 3 | 4 | 0 | 4 | 0 | 4 |
| 199 | 1 | 4 | 0 | 0 | 0 | 0 |
| 200 | 2–3 | 3 | 1 | 2 | 1 | 0 |
| 201 | 0 | 0 | 0 | 1 | 2 | 0 |
| 202 | 1 | 3 | 0 | 0 | 0 | 0 |
| 203 | 4 | 4 | 1 | 2 | 2 | 4 |
| 204 | 2 | 2 | 2 | 1 | 0 | 0 |
| 205 | 3 | 4 | 2 | 3 | 0 | 2 |
| 206 | 3 | 4 | 2 | 1 | 0 | 0 |
| 207 | 3 | 4 | 3 | 0 | 0 | 0 |
| 208 | 2 | 3 | 3 | 0 | 0 | 0 |
| 209 | 4 | 4 | 0 | 3 | 0 | 4 |
| 210 | 4 | 4 | 0 | 3 | 0 | 4 |
| 211 | 4 | 4 | 0 | 3 | 2 | 4 |
| 212 | 1 | 2 | 0 | 2 | 2 | 1 |
| 213 | 4 | 4 | 2 | 3 | 0 | 4 |
| 214 | 0 | 3 | 0 | 2 | 0 | 0 |
| 215 | 4 | 4 | 0 | 3 | 4 | 0 |
| 216 | 4 | 4 | 0 | 3 | 0 | 4 |
| 217 | 2 | 4 | 0 | 3 | 0 | 4 |
| 218 | 2 | 0 | 0 | 1 | 0 | 0 |
| 219 | 4 | 4 | 3 | 3 | 0 | 4 |
| 220 | 4 | 4 | 2 | 3 | 0 | 3 |
| 221 | 4 | 4 | 3 | 4 | 0 | 4 |
| 222 | 4 | 4 | 3 | 3 | 0 | 4 |
| 223 | 0 | 0 | 0 | 1 | 0 | 0 |
| 224 | 0 | 0 | 1 | 1 | 0 | 0 |
| 225 | 2 | 0 | 0 | 1 | 1 | 0 |
| 226 | 4 | 3 | 0 | 3 | 0 | 4 |
| 227 | 0 | 3 | 0 | 1 | 0 | 3 |
| 228 | 0 | 0 | 0 | 1 | 0 | 0 |
| 229 | 0 | 0 | 0 | 1 | 0 | 0 |
| 230 | 0 | 3 | 1 | 1 | 0 | 0 |
| 231 | 0 | 0 | 1 | 2 | 0 | 0 |
| 232 | 0 | 0 | 0 | 3 | 0 | 2 |
| 233 | 0 | 0 | 2 | 1 | 0 | 2 |
| 234 | 0 | 0 | 0 | 0 | 1 | 0 |
| 235 | 3 | 0 | 0 | 1 | 3 | 3 |
| 236 | 2 | 3 | 0 | 2 | 3 | 1 |
| 237 | 3 | 0 | 0 | 2 | 0 | 0 |
| 238 | 0 | 0 | 0 | 2 | 0 | 0 |
| 239 | 0 | 0 | 0 | 0 | 0 | 1 |
| 240 | 0 | 0 | 0 | 1 | 0 | 0 |
| 241 | 2 | 0 | 0 | 2 | 3 | 2 |
| 242 | 3 | 0 | 0 | 2 | 1 | 3 |
| 243 | 0 | 0 | 1 | 0 | 0 | 0 |
| 244 | 0 | 0 | 0 | 4 | 0 | 0 |
| 245 | 1 | 3 | 3 | 4 | 2 | 1 |
| 246 | 0 | 0 | 1 | 3 | 3 | 0 |
| 247 | 0 | 0 | 0 | 3 | 1 | 0 |
| 248 | 0 | 0 | 0 | 4 | 1 | 2 |
| 249 | 0 | 0 | 0 | 1 | 0 | 2 |
| 250 | 0 | 1 | 3 | 0 | 0 | 1 |
| 251 | 0 | 0 | 0 | 1 | 0 | 1 |
| 252 | 0 | 0 | 2 | 0 | 0 | 0 |
| 253 | 0 | 1 | 0 | 0 | 1 | 0 |
| 254 | 0 | 0 | 3 | 0 | 0 | 0 |

EXAMPLE 31

The thienopyrimidine derivatives were tested against a variety of foliage-borne bacterial plant diseases in the glasshouse. The anti-bacterial screening method employed a mist propagator to aid infection of treated plants by providing conditions of high humidity.

The plants were sprayed and/or root drenched with an aqueous solution containing 100 parts per million of the test chemical. After 48 hours they were inoculated with the appropriate disease organism. Inoculations were accompanied by wounding the plants, which was necessary for bacterial infection to take place. Immediately afterwards the plants were placed under high humidity. Agrimycin (17% Streptomycin sulphate) at 2000 p.p.m. and 100 p.p.m. was applied as a standard treatment and with water as a control. After eight days, the symptoms were assessed on a 0–4 scale given in the Table below, wherein the extent of the disease is given in the form of a grading as follows:

| Grading | Percentage Amount of Disease |
|---|---|
| 0 | 61 to 100 |
| 1 | 26 to 60 |
| 2 | 6 to 25 |
| 3 | 0 to 5 |
| 4 | No disease | and the disease code of Table 5 is given below:

| Disease and Plant | Disease Code |
|---|---|
| Xanthomonas oryzae (basterial blight of rice) | A |
| Erwinia amylovora (fireblight on pears) | B |

TABLE 5

| COMPOUND NO. | DISEASE CODE LETTER | |
| | A | B |
|---|---|---|
| 2 | 1 | 0 |
| 5 | 0–2 | 0 |
| 7 | 2 | 0–3 |
| 8 | 2 | 2 |
| 10 | 2 | 1 |
| 27 | 0 | 0–3 |

EXAMPLE 32

Compound Nos. 2, 3, 5 and 6 gave activity in a test conducted against tomato mosaic virus. Gradings (on a scale similar to those of Examples 15 and 16) were, respectively 1, 1, 2 and 4.

EXAMPLE 33

The activity of the thienopyrimidine having the formula:

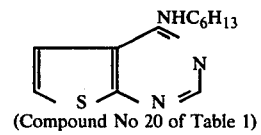

(Compound No 20 of Table 1)

was tested against a viriety of insect and other invertebrate pests. The compound was used in the form of a liquid preparation containing 0.1% by weight of the compound. The preparation was made by disolving the compound in a mixture of solvents consisting of 4 parts by volume of acetone and 1 part by volume of diacetone alcohol. The solutions were then diluted with water containing 0.01% by weight of a wetting agent sold under the trade name "LISSAPOL" NX until the liquid preparations contained the required concentration of the compound. "Lissapol" is a Trade Mark.

the test procedure adopted with regard to each pest was basically the same and comprised supporting a number of the pests on a medium which was usually a host plant or a foodstuff on which the pests feed, and treating either or both the pests and the medium with the preparations.

The mortality of the pests was then assessed at periods usually varying from one to three days after the treatment.

the results of the tests are given below in Table 6. In this Table the first column indicates the name of the pest species. Each of the subsequent columns indicates the host plant or medium on which it was supported, the number of days which were allowed to elapse after the treatment before assessing the mortality of the pests, and the results obtained for the compound. The assessment is expressed in integers which range from 0–3.

0 represents less than 30% kill
1 represents 30–49% kill
2 represents 50–90% kill
3 represents over 90% kill

TABLE 6

| PEST SPECIES | SUPPORT MEDIUM | NO. OF DAYS | GRADING |
|---|---|---|---|
| *Tetranychus telarius* (red spider mites; adults) | French Bean | 3 | 3 |
| *Aphis fabae* (aphids) | Broad Bean | 2 | 3 |
| *Megoura viceae* (aphids) | Broad Bean | 2 | 3 |

EXAMPLE 34

This Example illustrates the activity of the compounds and compositions of the invention against the disease apple powdery mildew, *Podosphaera leucotricha;* and vine powdery mildew, *Uncinula necator.*

Small apple (Jonathan) and vine plants about 3 weeks old and growing in mini pots measuring 3 centimeters in diameter were infected by placing them in an enclosed space and allowing spores of the disease blown into the still space to settle upon then over a period of about four to six hours.

Both "eradicant", "protectant" and "systemic" type tests were carried out. In the former the plants were inoculated with spores of the disease and then held in the glasshouse (apples) or a growth room (vines) under conditions conducive to disease development for two days before treatment, by spraying, with a solution or suspension of the test chemical containing 50 parts per million of the chemical. The plants were then allowed to dry over 24 hours and then returned to the glasshouse, under conditions conducive to disease development.

In the "protectant" type tests the plants were sprayed first with the test chemical (50 p.p.m.), allowed to dry overnight in a growth room and then infected, as described above, on the following day with spores of the disease.

In the "systemic" tests the plants in the pots were stood in 10 milliliter aliquots of solutions or suspensions of the test chemical (50 p.p.m.) and allowed to suck this up into the soil in the pots over a period of 24 to 48 hours. Four days later the plants were infected, as described above, with spores of the disease.

Assessment was made of the percentage amount of disease on the leaves of the plants (8 days for apples–9 to 10 days for vines) and the results expressed as a grading corresponding to a percentage range as in Example 30.

TABLE 7

| COMPOUND NO. (TABLE NO 1) | DISEASE | | | | | |
|---|---|---|---|---|---|---|
| | APPLE POWDERY MILDEW | | | VINE POWDERY MILDEW | | |
| | ERADICANT | PROTECTANT | SYSTEMIC | ERADICANT | PROTECTANT | SYSTEMIC |
| 5 | 2 | 1 | 4 | 0 | 3 | 0 |
| 7 | 4 | 4 | 1 | 1 | 1 | 0 |
| 11 | 4 | 1 | 0 | 2 | 0 | 0 |
| 20 | 2 | 4 | 1 | 2 | 1 | 0 |
| 21 | 4 | 4 | 0 | 2 | 2 | 0 |
| 32 | 4 | 0 | 3 | 1 | 3 | 0 |
| 40 | 4 | 4 | 2 | 3 | 2 | 0 |
| 44 | 4 | 4 | 2 | 2 | 2 | 2 |
| 47 | 4 | 0 | 1 | 1 | 1 | 2 |
| 56 | 4 | 4 | 0 | 1 | 1 | 0 |
| 57 | 2 | 2 | 0 | 0 | 1 | 0 |
| 88 | 2 | 4 | 0 | 2 | 4 | 0 |
| 73 | 0 | 0 | 4 | 1 | 0 | 0 |
| 79 | 1 | 1 | 2 | 4 | 1 | 0 |
| 82 | 1 | 0 | 4 | 4 | 1 | 0 |
| 83 | 1 | 0 | 2 | 4 | 1 | 0 |
| 84 | 3 | 1 | 0 | 2 | 0 | 0 |
| 87 | 2 | 4 | 1 | 1 | 1 | 0 |
| 88 | 3 | 4 | 1 | 1 | 1 | 0 |
| 89 | 3 | 4 | 0 | 2 | 4 | 0 |
| 93 | 2 | 1 | 4 | 2 | 1 | 0 |
| 107 | 4 | 3 | 0 | 2 | 2 | 0 |
| 121 | 2 | 3 | 0 | 4 | 0 | 0 |
| 148 | 0 | 0 | 0 | 4 | 0 | 0 |

EXAMPLE 35

This Example illustrates the activity of the invention compounds and the compositions against the disease black spot on roses, *Diplocarpon rosae.*

Rose plants (variety Elizabeth of Glamis) were grown in pots in a cool glasshouse.

Leaflets from vegetative shoots of the plants are cut off the laid undersurface down on damp filter papers in petri dishes, one pair of leaflets per dish.

The leaflets are then sprayed to run off with a fine spray of a solution or suspension of the test chemical 950 p.p.m.) and then allowed to dry off in a growth room for 4 to 6 hours. The lids are then placed over the dishes. The following day the leaflets are infected by spraying them with a suspension of spores of the disease containing 20,000 spores per milliliter.

The lids of the dishes are immediately replaced and the dishes held at 19° C. in high humidity for 24 hours before being returned to a growth room for disease to develop.

Disease is assessed approximately 7 days later as a percentage area of leaf infected, the result being expressed as a grading as described and set out in Example 30.

TABLE 8

| COMPOUND NO (TABLE 1) | DISEASE GRADING |
|---|---|
| 11 | 2 |
| 20 | 4 |
| 24 | 4 |
| 26 | 3 |
| 32 | 3 |
| 40 | 4 |
| 44 | 4 |
| 47 | 4 |
| 56 | 3 |
| 62 | 4 |
| 88 | 3 |
| 89 | 4 |
| 93 | 4 |
| 107 | 4 |
| 117 | 4 |
| 119 | 4 |
| 121 | 4 |

EXAMPLE 36

This Example illustrates the activity of the compositions and compounds of this invention against the following diseases:

| Fungal Disease | Plant Variety |
|---|---|
| *Erysiphe graminis tritici* (Egt) | Maris Butler wheat |
| *Erysiphe graminis hordei* (Egh) | Proctor Barley |
| *Puccinia recondita* (Pr) | Cardinal wheat |

The plants for this test were grown as described earlier in the preceding Examples. There were five plants per pot and the plants were 5 days old when sprayed with a solution or suspension of the test chemical. A separate and distinct set of plants in pots were 6 days old when root drenched, i.e. a solution or suspension of the test chemical applied to the soil in the pots.

The solution or suspension used to spray the plants contained 25 parts per million (p.p.m.) of the test chemical and 0.1% of a surface active agent. The spray was applied to the point of maximum retention of the solution by the foliage of the plants.

The solution or suspension used to separately root drench other pots was applied as 10 milliliter aliquots per pot and again contained 25 parts per million (p.p.m.) of the test chemical. There were two pots (replicates) per treatment.

In the test in which the plants were sprayed they were inoculated with spores of the disease 1 day after actual spraying. This period was 2 days for the tests in which the plants were root drenched. For the period between application of chemical and inoculation with the fungal pathogen the plants were kept in the room in which they were grown.

In the case of the disease *Puccinia recondita* only, the potted plants were placed in a humidity cabinet for 1 day.

Assessment was carried out after the following, tabulated, periods has elapsed after inoculation.

| DISEASE | NUMBER OF DAYS AFTER INOCULATION | |
|---|---|---|
| | SPRAY (PROTECTANT) | ROOT DRENCH (SYSTEMIC) |
| Egt and Egh | 8 | 7 |
| Pr | 10 | 9 |

The plants were meanwhile kept in the greenhouse. (Minimum temperature 17° C., maximum temperature 36° C.).

The results are as set out in the table below, the amount of disease being expressed in a grading corresponding to a percentage range of leaf surface infected as in Example 30.

TABLE 9

| COMPOUND NO (TABLE 1) | DISEASE | | | | | |
|---|---|---|---|---|---|---|
| | Egh | | Pr | | Egt | |
| | SPRAY | ROOT DRENCH | SPRAY | ROOT DRENCH | SPRAY | ROOT DRENCH |
| 5 | — | — | — | 3,4 | — | — |
| 24 | 4,3 | — | 4,4 | — | — | — |
| 30 | 3,0 | — | 3,3 | — | — | — |
| 32 | 0,0 | 3,3 | — | 3,3 | — | — |
| 33 | 3,2 | — | — | — | — | — |
| 35 | 3,4 | — | 3,4 | — | 3 | 0 |
| 40 | 2,1 | — | 4,4 | — | 4 | 0 |
| 56 | 0,1 | — | 3,3 | — | — | — |
| 61 | — | — | 3,2 | — | — | — |
| 74 | 3,2 | 0,0 | — | — | — | — |
| 79 | — | — | 3,3 | — | — | — |

"—"signifies not tested

EXAMPLE 37

The following compounds of Table No. 1 displayed activity in in vitro tests against fungi of economic importance.

4, 5, 11, 40, 44, 45, 49, 52, 59, 76, 77, 78, 128 and 178. Compounds Nos. 76 and 78 were especially active.

We claim:

1. A thienopyrimidine which in free base form has the formula:

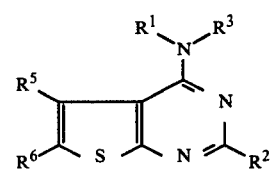

wherein $R^1$ is allyl, propargyl, a straight or branched chain alkyl of from 3 to 11 carbon atoms, a straight or branched chain alkyl group of 3 to 4 carbon atoms substituted with one or two hydroxy, cyano or methoxy, cycloalkyl of 3 to 8 carbon atoms, benzyl or benzyl substituted on the α carbon atom with a methyl group or in the ring with one to three methoxy or methyl groups or halogen atoms, dimethyl amino, phenylethyl, or tetrahydrofurfuryl; $R^3$ is hydrogen or $NH_2$; $R^2$ is hydrogen, methyl, ethyl chlorine, hydrazino or $N_3$; $R^5$ is hydrogen or methyl and $R^6$ is hydrogen, methyl or acetylamino or $R^5$ and $R^6$ together form a $-(CH_2)_4-$ bridging group; or an optical isomer thereof.

2. A thienopyrimidine which in free base form has the formula:

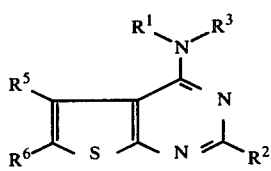

wherein $R^2$ is H, halogen, methyl, ethyl or hydrazino; $R^3$ is hydrogen or amino; $R^5$ and $R^6$ are hydrogen or methyl, and $R^1$ is a phenylmethyl or phenylethyl group a methoxy group or chlorine or fluorine atom; or an optical isomer thereof.

3. A thienopyrimidine according to claim 1 of the formula:

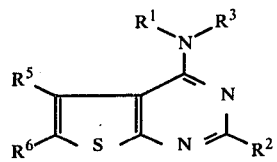

wherein $R^2$ is hydrogen, chlorine or methyl; $R^3$ is hydrogen; $R^5$ is hydrogen or methyl; $R^6$ is hydrogen; and $R^1$ is a straight or branched chain alkyl radical of from 3 to 11 carbon atoms, or an α-alkyl substituted benzyl radical substituted on the phenyl ring with from 1-3 chlorine or fluorine atoms and of up to 8 carbon atoms; or an optical isomer thereof.

4. A thienopyrimidine according to claim 1 of the formula:

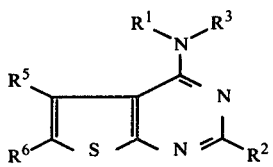

wherein $R^2$, $R^3$, $R^5$ and $R^6$ are hydrogen and $R^1$ is a straight or branched chain alky group of from 3 to 8 carbon atoms, or is an α-methyl substituted benzyl group; or an optical isomer thereof; or a salt thereof.

5. A thienopyrimidine according to claim 4 wherein $R^1$ is a branched chain alkyl group or an α-methyl substituted benzyl group.

6. A thienopyrimidine according to claim 5 wherein $R^2$, $R^3$, $R^5$ and $R^6$ are hydrogen and $R^1$ is $CH(CH_3)(CH_2)_5CH_3$.

* * * * *